United States Patent
Malhotra et al.

(10) Patent No.: US 11,257,012 B1
(45) Date of Patent: Feb. 22, 2022

(54) AUTOMATIC ANALYSIS OF PROCESS AND/OR OPERATIONS DATA RELATED TO A BENEFIT MANAGER ORGANIZATION

(71) Applicant: Accenture Global Solutions Limited, Dublin (IE)

(72) Inventors: Dinesh Malhotra, Naperville, IL (US); Milind Pawar, Saratoga, CA (US); Peter Westcott, Herndon, VA (US); Barbara Slagg, Ramsey, NJ (US)

(73) Assignee: Accenture Global Solutions Limited, Dublin (IE)

( * ) Notice: Subject to any disclaimer, the term of this patent is extended or adjusted under 35 U.S.C. 154(b) by 1218 days.

(21) Appl. No.: 15/685,784

(22) Filed: Aug. 24, 2017

Related U.S. Application Data

(60) Provisional application No. 62/517,622, filed on Jun. 9, 2017.

(51) Int. Cl.
*G06Q 10/06* (2012.01)
*G10L 15/18* (2013.01)
*G10L 15/22* (2006.01)
*G16H 40/20* (2018.01)

(52) U.S. Cl.
CPC ..... *G06Q 10/0631* (2013.01); *G06Q 10/0639* (2013.01); *G10L 15/18* (2013.01); *G10L 15/22* (2013.01); *G16H 40/20* (2018.01); *G10L 2015/223* (2013.01)

(58) Field of Classification Search
CPC .......... G06Q 10/0631; G06Q 10/0639; G10L 15/18; G10L 15/22; G10L 2015/223
See application file for complete search history.

(56) References Cited

U.S. PATENT DOCUMENTS

| | | | | |
|---|---|---|---|---|
| 6,101,479 | A | * | 8/2000 | Shaw ..................... G06Q 10/06 705/7.12 |
| 6,850,892 | B1 | * | 2/2005 | Shaw ..................... G06Q 10/06 705/7.26 |
| 7,761,316 | B2 | * | 7/2010 | Ligon .................... G06Q 10/10 705/7.29 |
| 10,417,597 | B2 | * | 9/2019 | Flores .................. G06Q 10/067 |
| 2004/0176980 | A1 | * | 9/2004 | Bulitta ................... G16H 40/20 705/2 |
| 2006/0184408 | A1 | * | 8/2006 | Giancola .......... G06Q 10/06375 705/7.37 |

(Continued)

*Primary Examiner* — Vivek D Koppikar
(74) *Attorney, Agent, or Firm* — Harrity & Harrity, LLP

(57) ABSTRACT

A device may receive data associated with a benefit manager organization. The data may relate to a performance of the benefit manager organization and hardware resources associated with the benefit manager organization. The device may process the data using a technique after receiving the data. The device may map the data to a benefit manager operating model based on processing the data. The benefit manager operating model may identify a functional area or a sub-area of another benefit manager organization. The device may perform an analysis of the data based on mapping the data to the benefit manager operating model. The device may identify a deficiency related to the performance of the benefit manager organization. The device may perform an action to positively impact the performance of the benefit manager organization based on identifying the deficiency. The action may reduce the deficiency.

20 Claims, 23 Drawing Sheets

(56) References Cited

U.S. PATENT DOCUMENTS

| | | | |
|---|---|---|---|
| 2012/0204103 A1* | 8/2012 | Stevens | G06Q 10/10 |
| | | | 715/273 |
| 2012/0284316 A1* | 11/2012 | Klinker | G06Q 10/067 |
| | | | 707/822 |
| 2013/0326531 A1* | 12/2013 | Kenkre | G06Q 10/087 |
| | | | 718/104 |
| 2017/0061558 A1* | 3/2017 | Kogut-O'Connell | |
| | | | G06N 5/022 |
| 2018/0357587 A1* | 12/2018 | Bogaert | G06Q 10/0631 |
| 2019/0205378 A1* | 7/2019 | Tripathi | G06F 40/30 |

\* cited by examiner

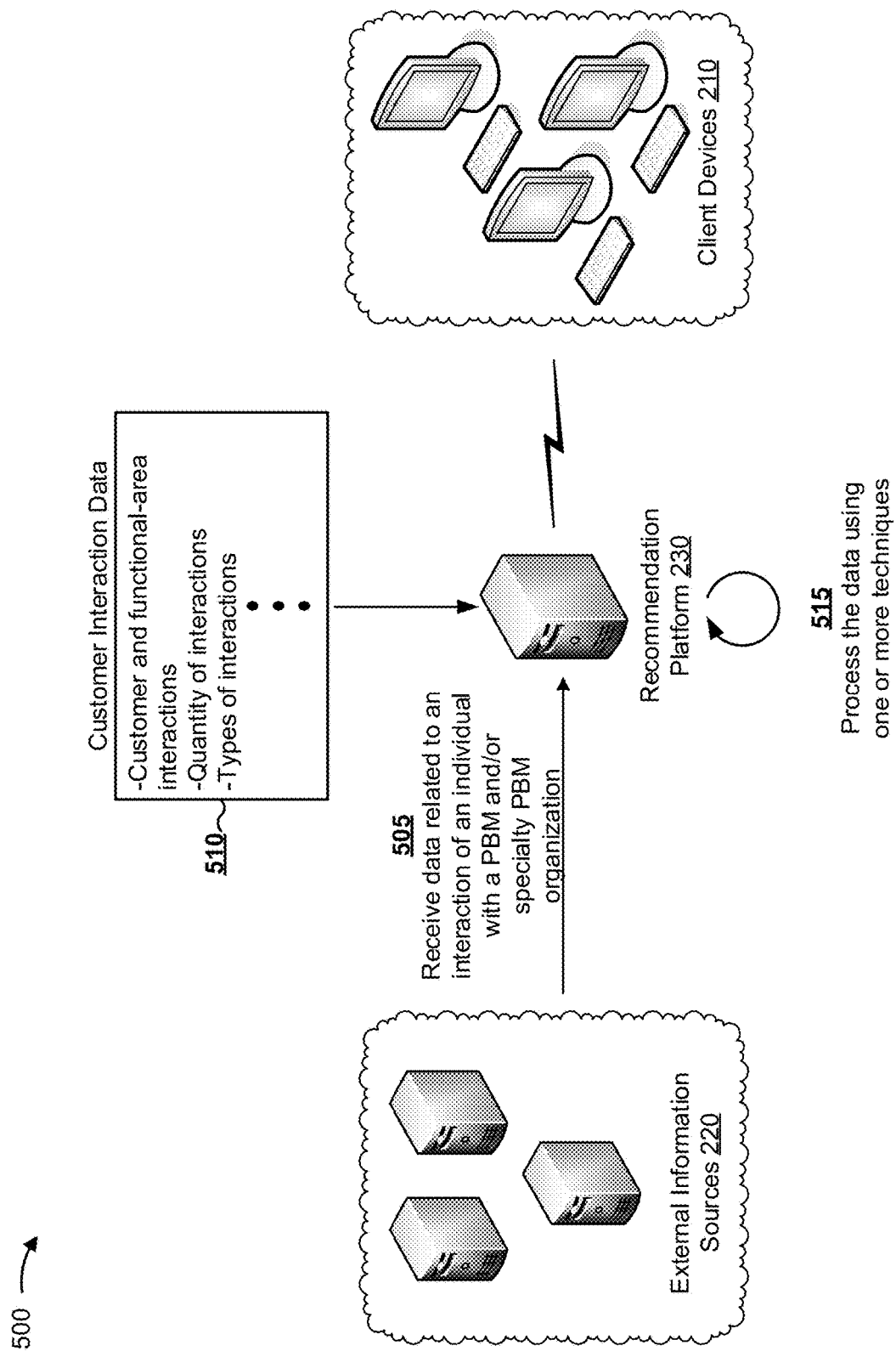

AUTOMATIC ANALYSIS OF PROCESS AND/OR OPERATIONS DATA RELATED TO A BENEFIT MANAGER ORGANIZATION

RELATED APPLICATION(S)

This application claims priority under 35 U.S.C. § 119 to U.S. Provisional Patent Application No. 62/517,622, filed on Jun. 9, 2017, the content of which is incorporated by reference herein in its entirety.

BACKGROUND

A process may include a set of interrelated activities that interact to achieve a result. For example, a benefit manager organization, such as a pharmacy benefit manager (PBM) and/or a specialty PBM organization may implement a process related to operations of the benefit manager organization, patients associated with the benefit manager organization, and/or the like. A result of the process may be affected by a structure and/or organization of the process and/or benefit manager organization.

SUMMARY

According to some possible implementations, a device may include one or more processors to receive data associated with an organization. The data may relate to a performance of a process or operations of the organization. The data may relate to hardware resources of the organization used to implement the process or the operations. The one or more processors may process the data using a technique to permit an analysis of the data after receiving the data. The technique may include at least one of natural language processing, or speech-to-text processing. The one or more processors may map the data to an operating model based on processing the data. The operating model may be used to compare the organization to one or more other organizations. The one or more processors may perform the analysis of the data based on mapping the data to the operating model. The analysis may be used to identity a deficiency related to the organization. The one or more processors may identify an infrastructure of the organization based on performing the analysis of the data. The one or more processors may perform an action to positively impact the performance of the process or the operations of the organization after identifying the infrastructure of the organization. The action may positively impact the deficiency.

According to some possible implementations, a method may include receiving, by a device, data associated with a benefit manager organization. The data may relate to at least one of a process implemented by the benefit manager organization, or operations of the benefit manager organization. The method may include processing, by the device, the data using a technique to permit an analysis of the data after receiving the data. The technique may be used to format the data to permit mapping or analysis of the data. The method may include mapping, by the device, the data to a benefit manager operating model based on processing the data. The benefit manager operating model may be used to perform the analysis of the benefit manager organization. The benefit manager operating model may be associated with one or more other benefit manager organizations. The method may include performing, by the device, the analysis of the data based on mapping the data to the benefit manager operating model. The method may include identifying, by the device, an infrastructure of the organization based on performing the analysis. The method may include performing, by the device, an action to positively impact the performance of the process or the operations of the benefit manager organization based on performing the analysis.

According to some possible implementations, a non-transitory computer-readable medium may store one or more instructions that, when executed by one or more processors, cause the one or more processors to receive data associated with one or more benefit manager organizations. The data may relate to a performance of the one or more benefit manager organizations. The data may relate to one or more hardware resources associated with the one or more benefit manager organizations. The one or more instructions, when executed by the one or more processors, may cause the one or more processors to process the data using one or more techniques after receiving the data. The one or more instructions, when executed by the one or more processors, may cause the one or more processors to map the data to one or more benefit manager operating models based on processing the data. The one or more benefit manager operating models may identify one or more functional areas or one or more sub-areas of one or more other benefit manager organizations.

The one or more instructions, when executed by the one or more processors, may cause the one or more processors to perform one or more analyses of the data based on mapping the data to the one or more benefit manager operating models. The one or more instructions, when executed by the one or more processors, may cause the one or more processors to identify an infrastructure of the organization based on performing the one or more analyses. The one or more instructions, when executed by the one or more processors, may cause the one or more processors to identify one or more deficiencies related to the performance of the one or more benefit manager organizations or the infrastructure of the organization based on identifying the infrastructure. The one or more instructions, when executed by the one or more processors, may cause the one or more processors to perform one or more actions to positively impact the performance of the one or more benefit manager organizations based on identifying the one or more deficiencies. The one or more actions may reduce the one or more deficiencies.

BRIEF DESCRIPTION OF THE DRAWINGS

FIGS. 5A-5D are diagrams of an example implementation relating to the example process shown in FIG. 4;

DETAILED DESCRIPTION

The following detailed description of example implementations refers to the accompanying drawings. The same reference numbers in different drawings may identify the same or similar elements.

A benefit manager organization, such as a pharmacy benefit manager (PBM) organization and/or a specialty PBM organization may implement a process to perform a function of the benefit manager organization. For example, the benefit manager organization may implement a process to intake prescription requests, to manufacture (or place an order for) a prescription, and/or the like. The benefit manager organization may lack a technique for efficiently and accurately performing a computer-based analysis of a performance of the process and/or the benefit manager organization. In addition, the benefit manager organization may lack a technique for comparing the performance of the process and/or operations of the benefit manager organization to a threshold (e.g., a benchmark, an industry standard, or an organization identified as a high-performing benefit manager organization relative to other benefit manager organizations), such as to identify a deficiency related to the performance of the process and/or operations.

Implementations described herein provide a recommendation platform that is capable of receiving data associated with a performance of a process of a benefit manager organization and/or operations of the benefit manager organization, analyzing the data to identify a deficiency related to the performance of the process and/or operations and/or to identify a manner in which to improve the performance, and/or performing an action to positively impact the deficiency and/or to improve the performance.

In this way, some implementations, described herein, increase an efficiency of analyzing a process of a benefit manager organization and/or operations of the benefit manager organization. In addition, some implementations, described herein, improve an accuracy of a result and/or output of a process, thereby conserving processing resources that would otherwise be consumed due to inaccurate results and/or outputs. Further, some implementations, described herein, improve performance of a process and/or operations of a benefit manager organization, thereby conserving processing resources and/or computing resources of devices used to implement the process and/or the operations.

FIGS. 1A-1D are diagrams of an overview of an example implementation 100 described herein. As shown in FIGS. 1A-1D, example implementation 100 includes one or more external information sources, a recommendation platform, and one or more client devices.

Figure 1A:
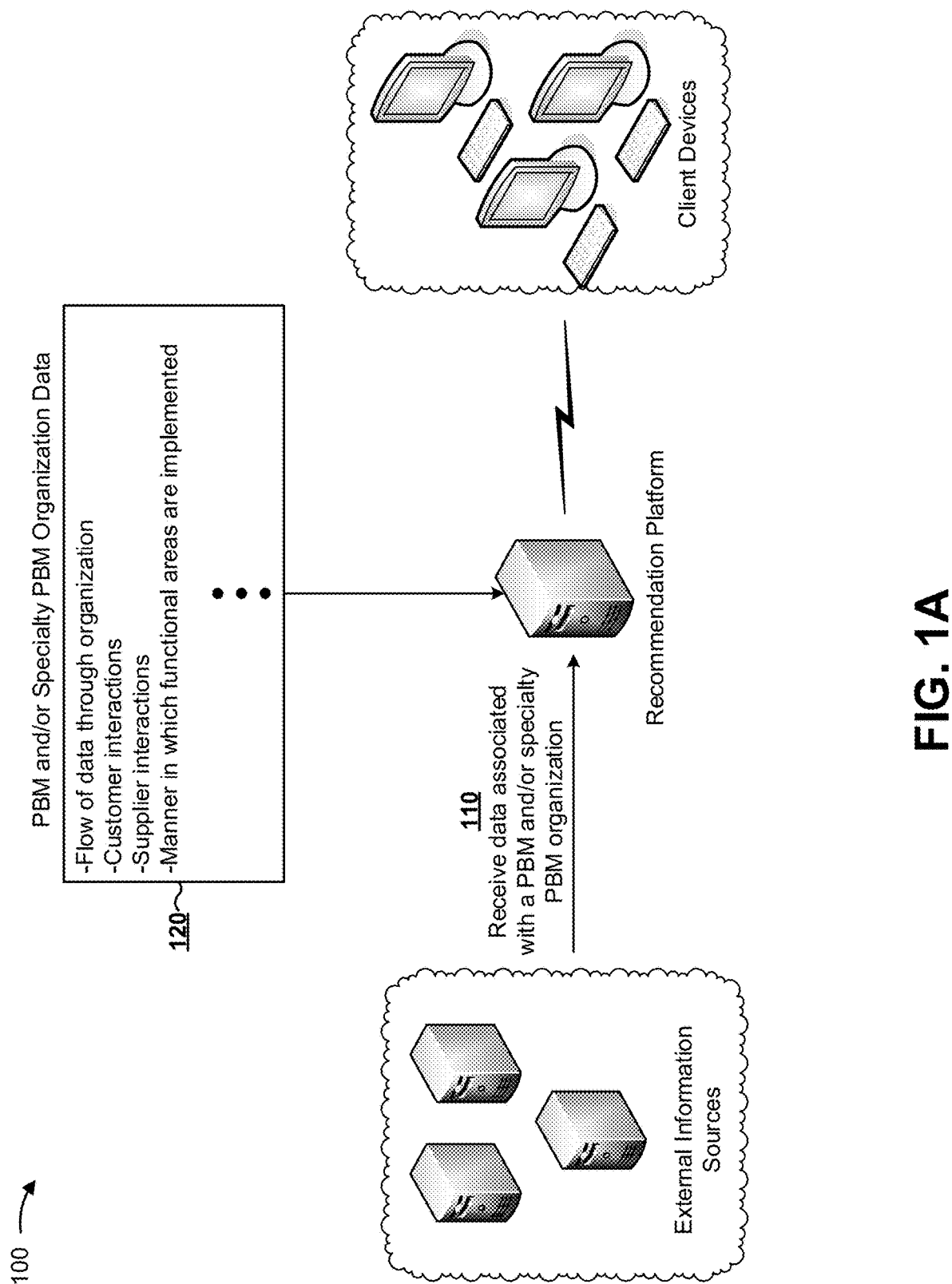
FIGS. 1A-1D are diagrams of an overview of an example implementation described herein.

As shown in FIG. 1A, and by reference number 110, the recommendation platform may receive, from the external information sources, data associated with a PBM and/or specialty PBM organization (e.g., PBM and/or specialty PBM organization data). For example, the PBM and/or specialty PBM organization data received may relate to performance of a process of the PBM and/or specialty PBM organization, may relate to operations of a PBM and/or specialty PBM organization, and/or the like. In some implementations, the recommendation platform may receive millions, billions, trillions, etc. of data elements when receiving the PBM and/or specialty PBM organization data.

As shown by reference number 120, the PBM and/or specialty PBM organization data may include data elements related to a flow of data through a PBM and/or specialty PBM organization, customer interactions with the PBM and/or specialty PBM organization, supplier interactions with the PBM and/or specialty PBM organization, a manner in which the PBM and/or specialty PBM organization implements functional areas, and/or the like. In some implementations, customer interaction data may include aggregated and/or anonymized data that may be encrypted according to an encryption technique.

Figure 1B:
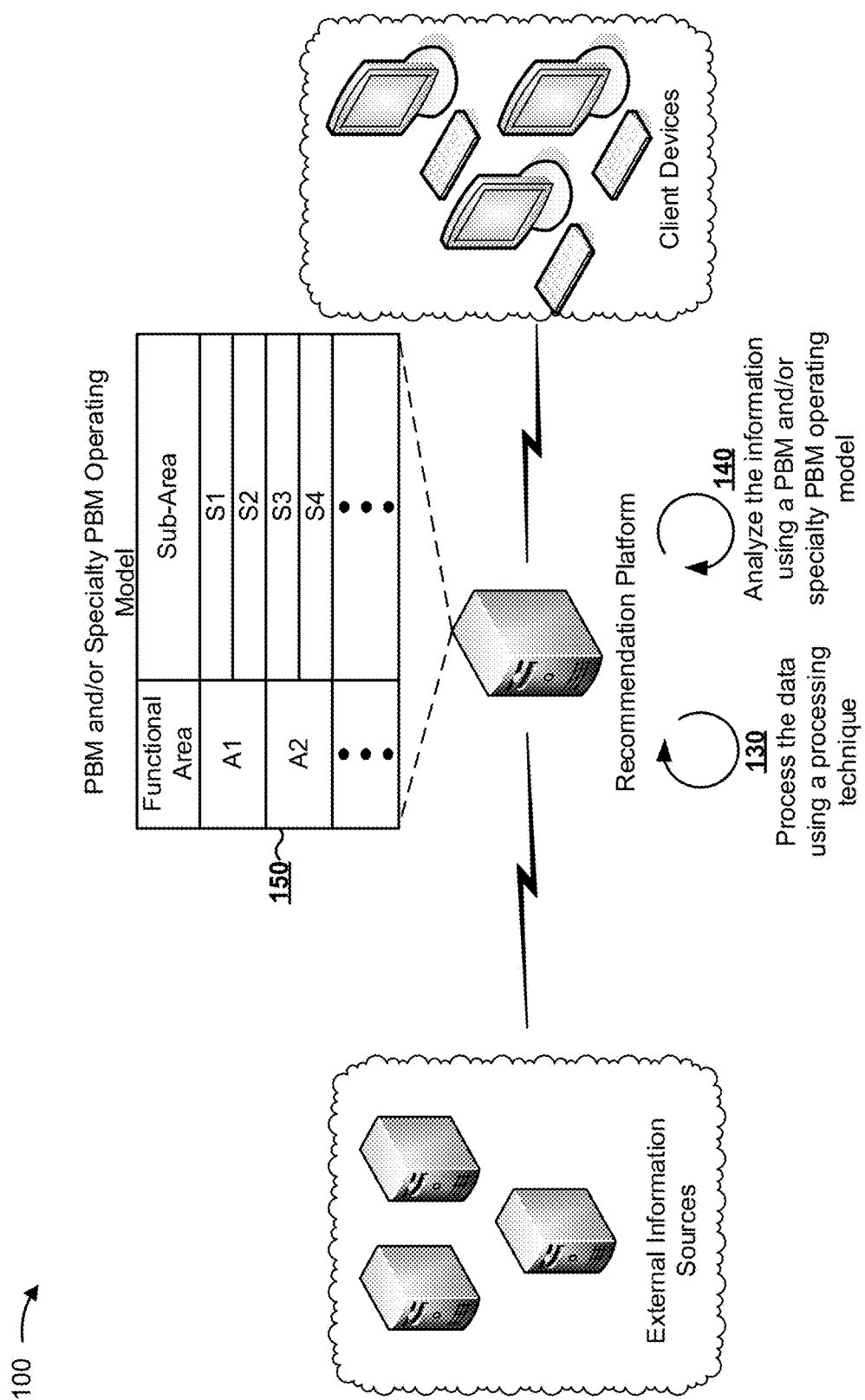

As shown in FIG. 1B, and by reference number 130, the recommendation platform may process the PBM and/or specialty PBM organization data using a processing technique. For example, the recommendation platform may process the data using natural language processing, artificial intelligence, machine learning, and/or the like.

As shown by reference number 140, the recommendation platform may analyze the PBM and/or specialty PBM organization data using a PBM and/or specialty PBM operating model. For example, the recommendation platform may map data to portions of the PBM and/or specialty PBM operating model to identify a manner in which the organization implements a process and/or operates. Additionally, or alternatively, and as another example, the recommendation platform may use the PBM and/or specialty PBM operating model to perform a comparison of the data and a threshold, such as to identify a deficiency of the PBM and/or specialty PBM organization relative to a benchmark or industry standard. In some implementations, the recommendation platform may analyze the data to identify a deficiency related to the performance of a process and/or operations of the PBM and/or specialty PBM organization.

An example of a PBM and/or specialty PBM operating model is shown by reference number 150. The PBM and/or specialty PBM operating model may represent a structure or organization of another PBM and/or specialty PBM organization (e.g., identified as a high-performing PBM and/or specialty PBM organization), a benchmark PBM and/or specialty PBM organization, a threshold, an industry standard, and/or the like. In some implementations, the PBM and/or specialty PBM operating model may identify functional areas of the PBM and/or specialty PBM organization (e.g., shown as A1, A2, etc.). For example, a functional area may relate to performing PBM operations, directing, planning, and/or guiding the PBM and/or specialty PBM organization, managing customer interactions, processes of the PBM and/or specialty PBM organization, and/or the like.

In some implementations, the operating model may identify sub-areas corresponding to a functional area (e.g., shown as S1 and S2 as sub-areas of functional area A1, and S3 and S4 as sub-areas of functional area A2). For example, sub-areas corresponding to managing customer interactions may include appeals, grievances, complaints, and customer service.

Figure 1C:
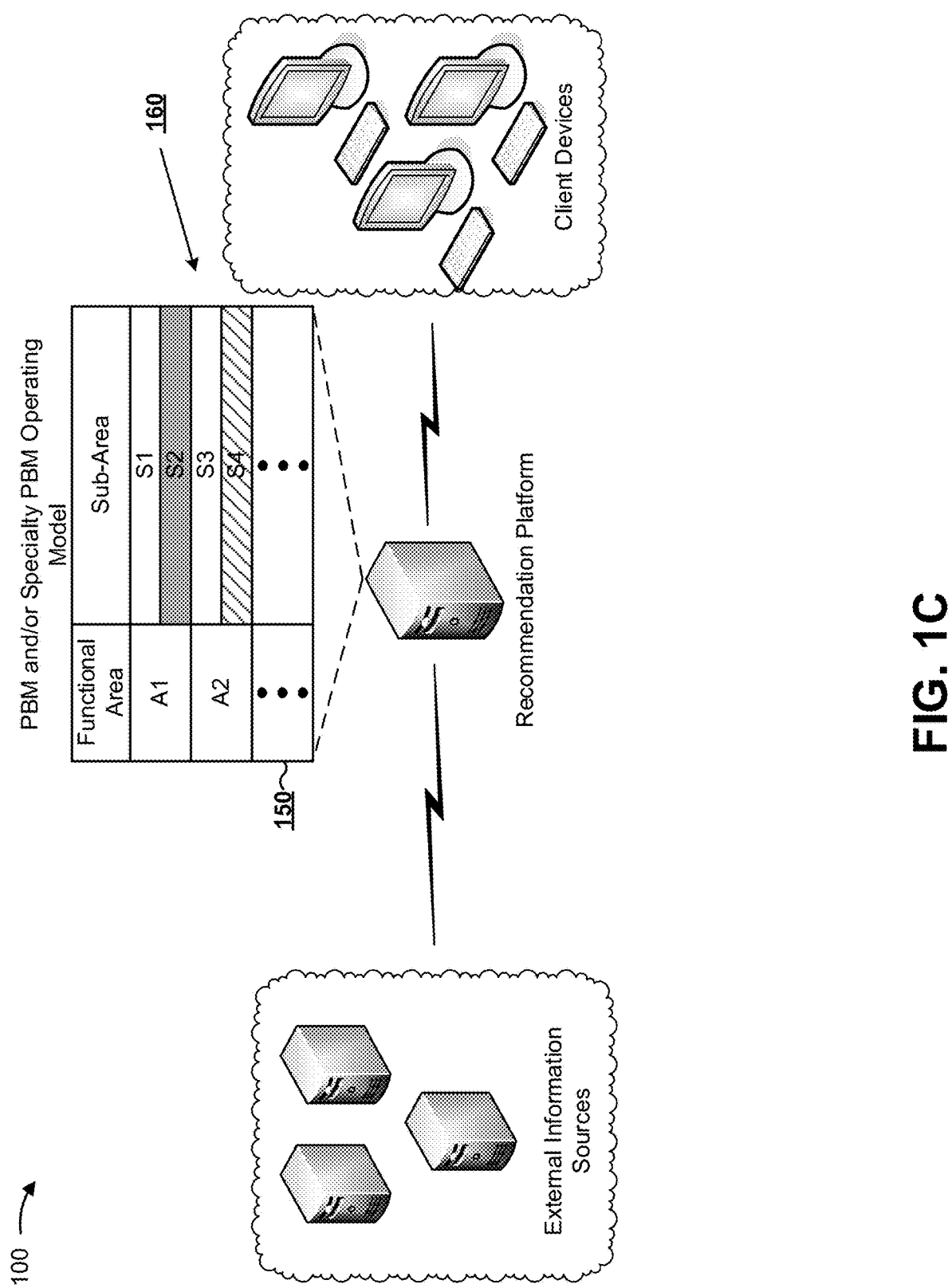

As shown in FIG. 1C, and by reference number 160, the recommendation platform may identify a deficiency related to performance of a process and/or operations of the PBM and/or specialty PBM organization and/or may identify a manner in which the PBM and/or specialty PBM organization can be improved. In some implementations, the recommendation platform may identify sub-areas without a deficiency (e.g., that satisfy a threshold or that do not satisfy a threshold that indicates a deficiency), as shown as white boxes (e.g., S1 and S3). In some implementations, the recommendation platform may identify sub-areas that have a deficiency (e.g., that satisfy a first threshold indicating a deficiency but not a second threshold indicating a more or less severe deficiency), as shown as a striped box (e.g., S4).

In some implementations, the recommendation platform may identify sub-areas that have a different deficiency (e.g., that satisfy a first threshold and a second threshold indicating a deficiency), as shown as a dark shaded box (e.g., S2). The recommendation platform may identify the deficiency using thresholds, information identifying an industry standard, and/or the like. In this way, the recommendation platform may identify a deficiency related to performance of a process and/or operations of a PBM and/or specialty PBM organization and/or identify a manner in which to improve the performance of the process and/or operations.

Figure 1D:
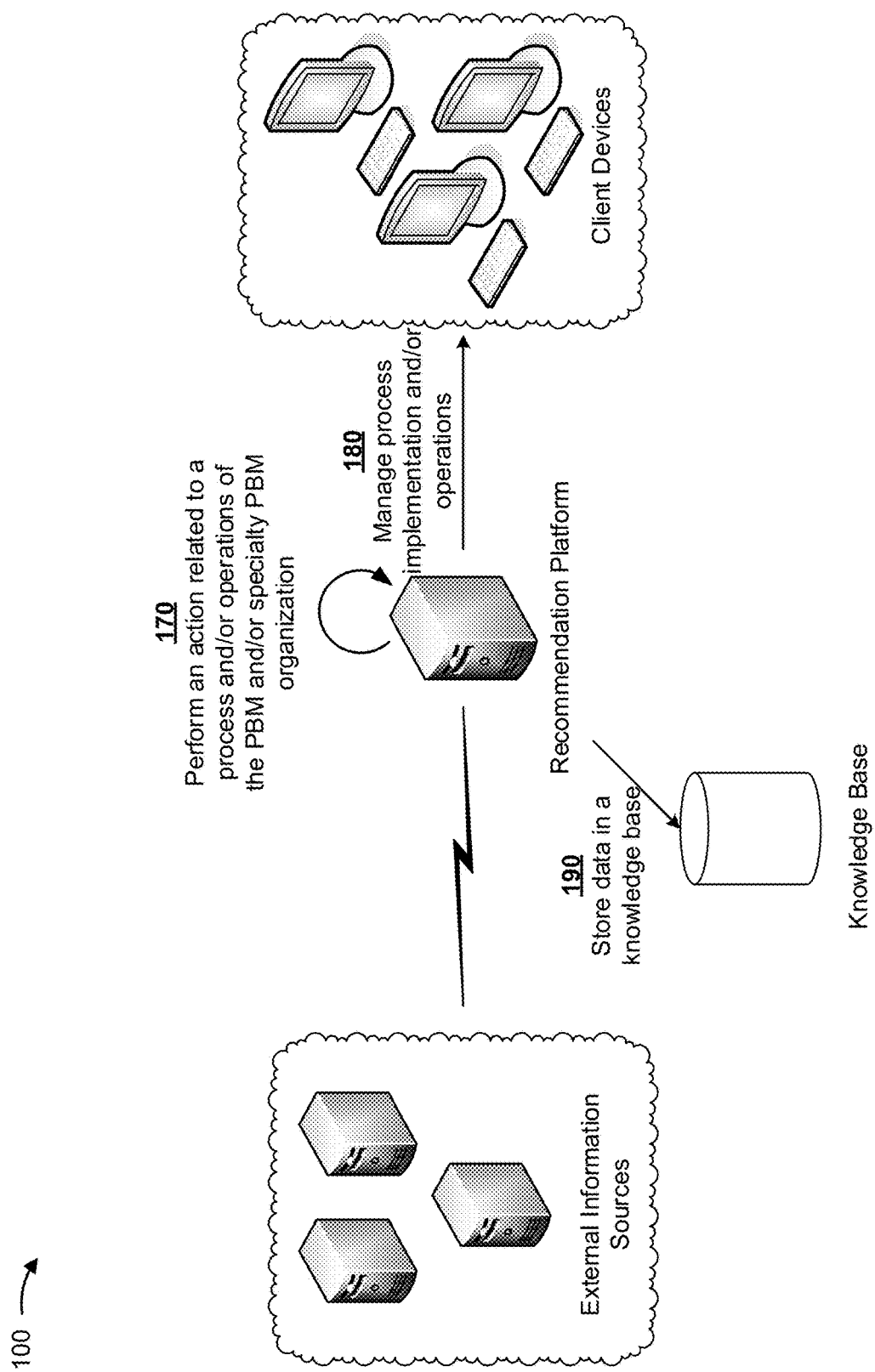

As shown in FIG. 1D, and by reference number 170, the recommendation platform may perform an action related to a process and/or operations of the PBM and/or specialty PBM organization. For example, the recommendation platform may perform an action to positively impact a deficiency related to performance of the process and/or operations of the PBM and/or specialty PBM organization. For example, the recommendation platform may perform an action to reduce or eliminate a deficiency, to increase an efficiency of a process and/or operations of the PBM and/or specialty PBM organization (e.g., thereby conserving processing resources of devices that the PBM and/or specialty PBM organization uses to implement the process and/or operations), and/or the like.

As shown by reference number 180, the recommendation platform may manage implementation of a process and/or operations of the PBM and/or specialty PBM organization. For example, the recommendation platform may provide a set of instructions to one or more client devices to perform a process in a particular manner. Additionally, or alternatively, and as another example, the recommendation platform may gather data, relating to metrics, from the client devices and may adjust performance of the process and/or operations of the organization based on the metrics. Continuing with the previous example, the recommendation platform may dynamically adjust the performance of the process and/or operations (e.g., in real-time or near real-time as the recommendation platform receives data).

As shown by reference number 190, the recommendation platform may store the data associated with the analysis in a knowledge base (e.g., a knowledge graph). Additionally, or alternatively, the recommendation platform may store data gathered during management of the process and/or operations of the PBM and/or specialty PBM organization. In some implementations, the knowledge base may include data from other analyses. For example, the recommendation platform may use the knowledge base to perform machine learning, data analysis, etc., to improve analysis of the process and/or operations.

In this way, some implementations, described herein, increase an efficiency of analyzing a process and/or operations of a PBM and/or specialty PBM organization. In addition, some implementations, described herein, improve an accuracy of a result and/or output of a process (e.g., by reducing a related deficiency), thereby conserving processing resources that would otherwise be consumed due to inaccurate results and/or outputs. Further, some implementations, described herein, improve performance of a process and/or operations of a PBM and/or specialty PBM organization, thereby conserving processing resources and/or computing resources of devices used to implement the process and/or the operations.

Implementations will be described in the context of a benefit manager organization (e.g., a PBM and/or a specialty PBM organization). These implementations equally apply to other kinds of organizations, such as organizations relating to manufacturing, construction, information technology, and/or the like.

As indicated above, FIGS. 1A-1D are provided merely as an example. Other examples are possible and may differ from what was described with regard to FIGS. 1A-1D. Although implementations were described with respect a PBM and/or specialty PBM organization, the implementations apply equally to other types of organizations, such as non-PBM and/or non-specialty PBM organizations that are performing PBM and/or specialty PBM-like functions, information technology organizations, manufacturing organizations, and/or the like.

Figure 2:
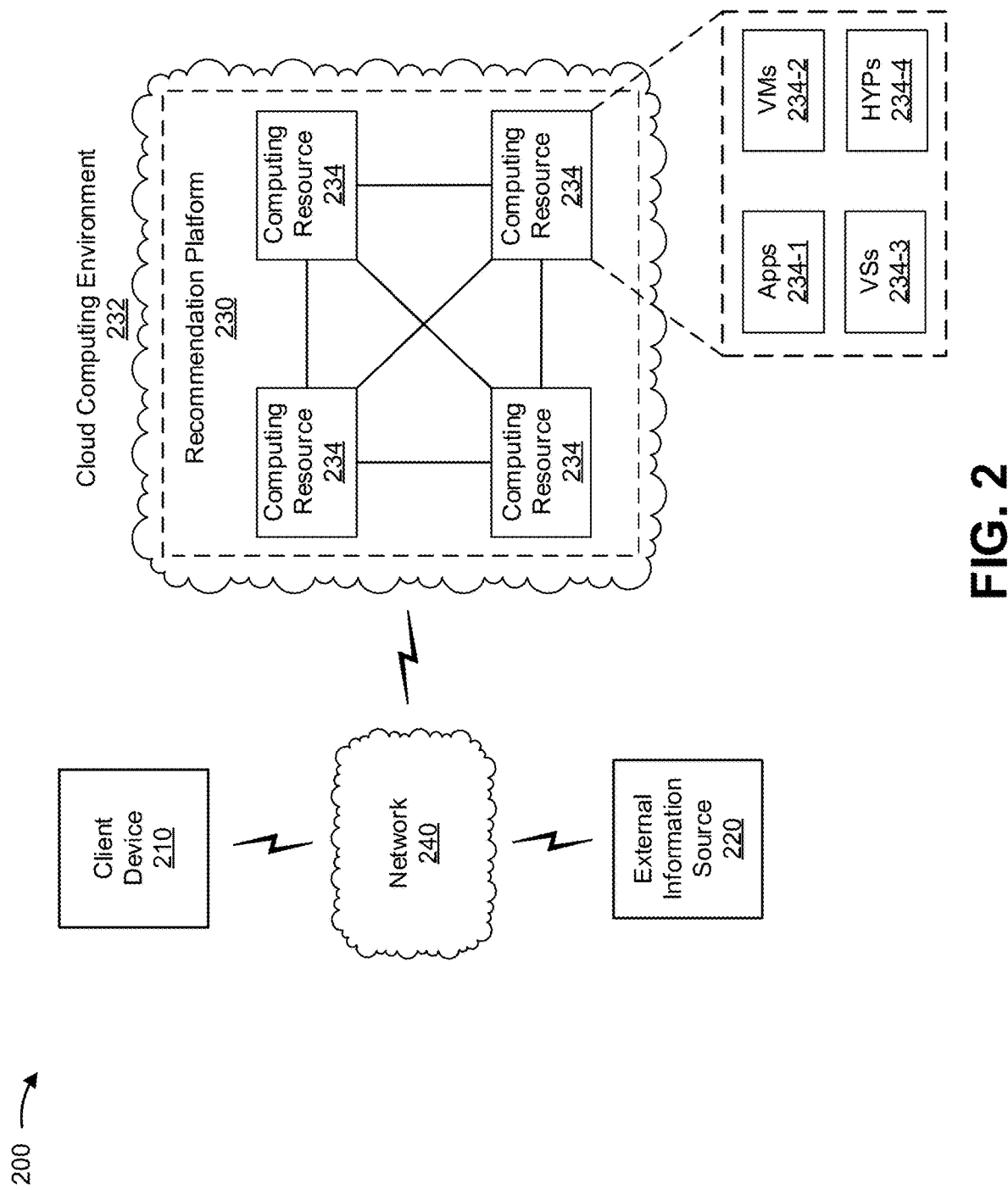
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include client device 210, external information source 220, recommendation platform 230, cloud computing environment 232, and a set of computing resources 234. Devices of environment 200 may interconnect via wired connections, wireless connections, or a combination of wired and wireless connections.

Client device 210 includes one or more devices capable of receiving, generating, storing, processing, and/or providing information associated with analyzing data related to a benefit manager organization. For example, client device 210 may include a desktop computer, a mobile phone (e.g., a smart phone or a radiotelephone), a laptop computer, a tablet computer, a gaming device, a wearable communication device (e.g., a smart wristwatch or a pair of smart eyeglasses), or a similar type of device. In some implementations, client device 210 may receive data associated with an analysis that recommendation platform 230 has performed, as described elsewhere herein. Additionally, or alternatively, client device 210 may provide information for display (e.g., information related to an analysis of data related to performance of a benefit manager organization), as described elsewhere herein.

External information source 220 includes one or more devices capable of receiving, generating, storing, processing, and/or providing information associated with an analysis of a benefit manager organization. For example, external information source 220 may include a server (e.g., in a data center or a cloud computing environment), a data center (e.g., a multi-server micro data center), a workstation computer, a virtual machine (VM) provided in a cloud computing environment, or a similar type of device. In some implementations, external information source 220 may provide, to recommendation platform 230, information related to performance of a process and/or operations of a benefit manager organization, as described elsewhere herein. Additionally, or alternatively, external information source 220 may store information related to an analysis of a benefit manager organization, as described elsewhere herein.

Recommendation platform 230 includes one or more devices capable of analyzing data related to a benefit manager organization. For example, recommendation platform 230 may include a cloud server or a group of cloud servers. In some implementations, recommendation platform 230 may be designed to be modular such that certain software components can be swapped in or out depending on a particular need. As such, recommendation platform 230 may be easily and/or quickly reconfigured for different uses.

In some implementations, as shown, recommendation platform 230 may be hosted in cloud computing environment 232. Notably, while implementations described herein describe recommendation platform 230 as being hosted in cloud computing environment 232, in some implementations, recommendation platform 230 may not be cloud-based (i.e., may be implemented outside of a cloud computing environment) or may be partially cloud-based.

Cloud computing environment 232 includes an environment that hosts recommendation platform 230. Cloud computing environment 232 may provide computation, software, data access, storage, and/or other services that do not require end-user knowledge of a physical location and configuration of a system and/or a device that hosts recommendation platform 230. As shown, cloud computing environment 232 may include a group of computing resources 234 (referred to collectively as "computing resources 234" and individually as "computing resource 234").

Computing resource 234 includes one or more personal computers, workstation computers, server devices, or another type of computation and/or communication device. In some implementations, computing resource 234 may host recommendation platform 230. The cloud resources may include compute instances executing in computing resource 234, storage devices provided in computing resource 234, data transfer devices provided by computing resource 234, etc. In some implementations, computing resource 234 may communicate with other computing resources 234 via wired connections, wireless connections, or a combination of wired and wireless connections.

As further shown in FIG. 2, computing resource 234 may include a group of cloud resources, such as one or more applications ("APPs") 234-1, one or more virtual machines ("VMs") 234-2, one or more virtualized storages ("VSs") 234-3, or one or more hypervisors ("HYPs") 234-4.

Application 234-1 includes one or more software applications that may be provided to or accessed by one or more devices of environment 200. Application 234-1 may eliminate a need to install and execute the software applications on devices of environment 200. For example, application 234-1 may include software associated with recommendation platform 230 and/or any other software capable of being provided via cloud computing environment 232. In some implementations, one application 234-1 may send/receive information to/from one or more other applications 234-1, via virtual machine 234-2.

Virtual machine 234-2 includes a software implementation of a machine (e.g., a computer) that executes programs like a physical machine. Virtual machine 234-2 may be either a system virtual machine or a process virtual machine, depending upon use and degree of correspondence to any real machine by virtual machine 234-2. A system virtual machine may provide a complete system platform that supports execution of a complete operating system ("OS"). A process virtual machine may execute a single program, and may support a single process. In some implementations, virtual machine 234-2 may execute on behalf of a user (e.g., a user of client device 210), and may manage infrastructure of cloud computing environment 232, such as data management, synchronization, or long-duration data transfers.

Virtualized storage 234-3 includes one or more storage systems and/or one or more devices that use virtualization techniques within the storage systems or devices of computing resource 234. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 234-4 provides hardware virtualization techniques that allow multiple operating systems (e.g., "guest operating systems") to execute concurrently on a host computer, such as computing resource 234. Hypervisor 234-4 may present a virtual operating platform to the guest operating systems, and may manage the execution of the guest operating systems. Multiple instances of a variety of operating systems may share virtualized hardware resources.

Network 240 includes one or more wired and/or wireless networks. For example, network 240 may include a cellular network (e.g., a long-term evolution (LTE) network, a code division multiple access (CDMA) network, a 3G network, a 4G network, a 5G network, or another type of cellular network), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
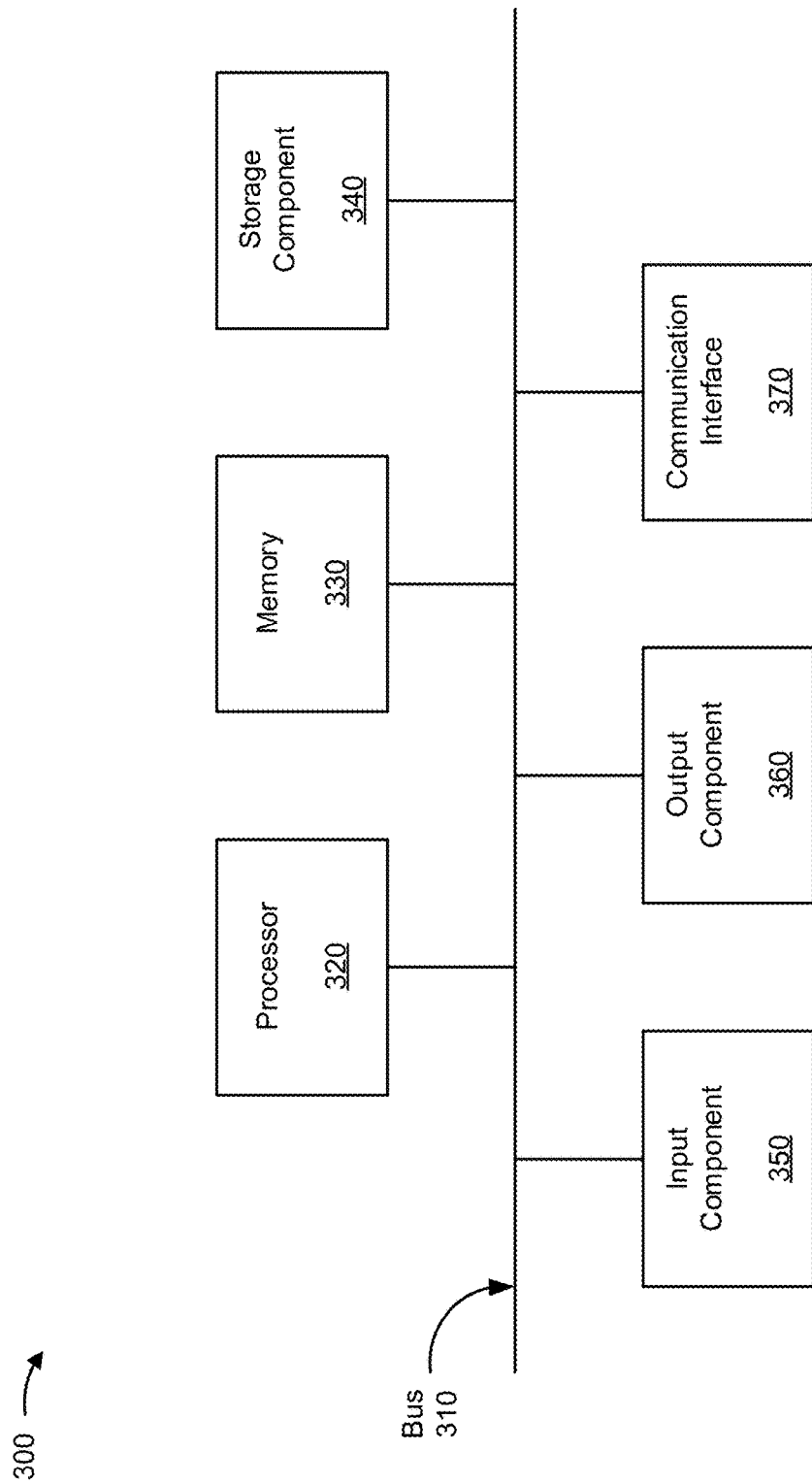
FIG. 3 is a diagram of example components of one or more devices of FIG. 2.

FIG. 3 is a diagram of example components of a device 300. Device 300 may correspond to client device 210, external information source 220, and/or recommendation platform 230. In some implementations, client device 210, external information source 220, and/or recommendation platform 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operations and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
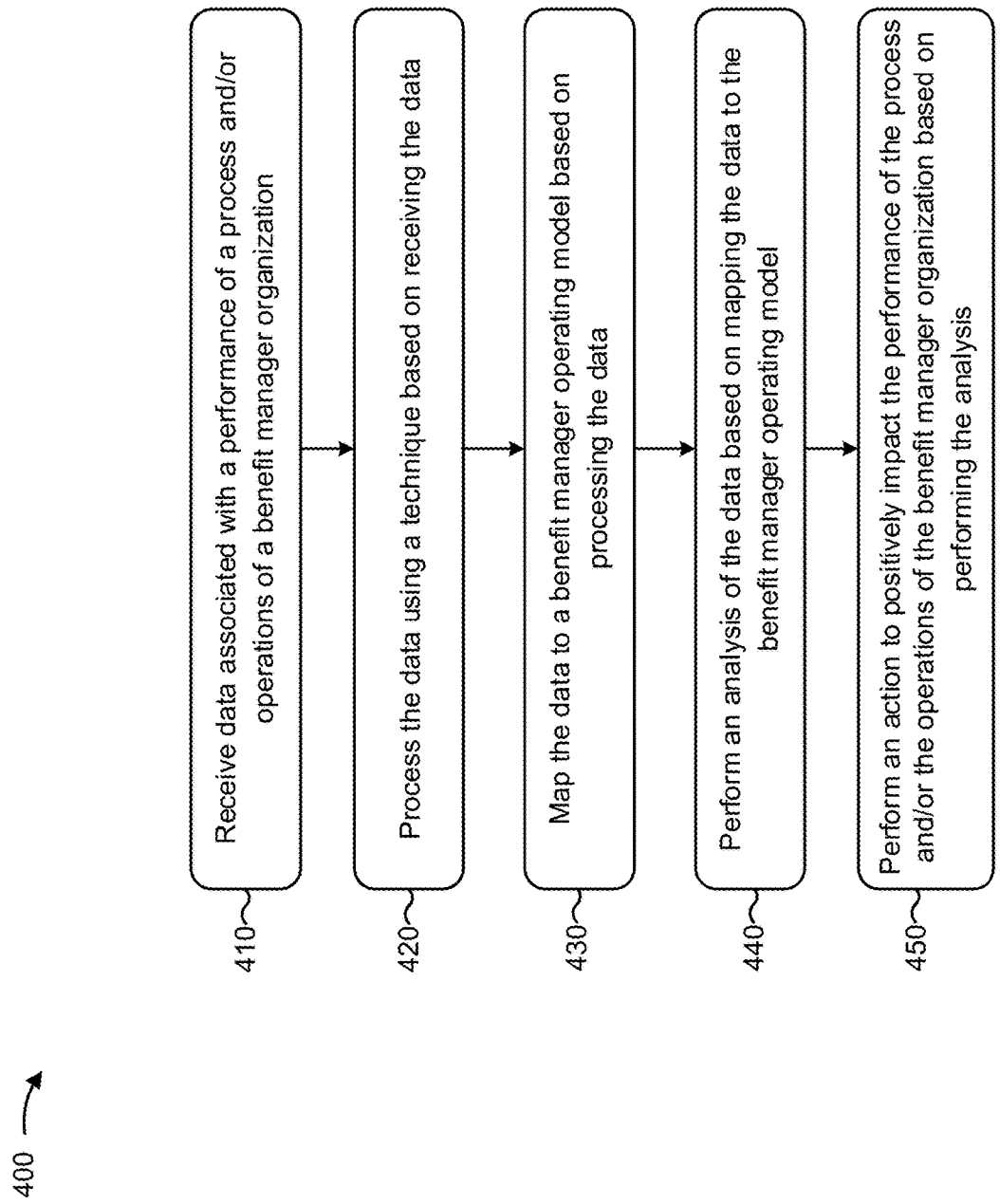
FIG. 4 is a flow chart of an example process for automatic analysis of process and/or operations data related to a benefit manager organization.

FIG. 4 is a flow chart of an example process 400 for automatic analysis of process and/or operations data related to a benefit manager organization. In some implementations, one or more process blocks of FIG. 4 may be performed by recommendation platform 230. In some implementations, one or more process blocks of FIG. 4 may be performed by another device or a group of devices separate from or including recommendation platform 230, such as client device 210 and external information source 220.

As shown in FIG. 4, process 400 may include receiving data associated with a performance of a process and/or operations of a benefit manager organization (block 410). For example, recommendation platform 230 may receive data associated with a performance of a process and/or operations of a benefit manager organization. In some implementations, recommendation platform 230 may receive the data periodically, according to a schedule, based on input from a user of client device 210, based on requesting the data, and/or the like. In some implementations, recommendation platform 230 may receive the data from external information source 220.

In some implementations, the data may relate to a benefit manager organization, such as a PBM and/or a specialty PBM organization. For example, the data may relate to an organization that is a third-party administrator of prescription drug programs for a commercial health plan, a self-insured employer plan, a Medicare Part D plan, a state or federal government employee plan, and/or the like.

In some implementations, the data may relate to a performance of a process of the benefit manager organization and/or operations of a benefit manager organization. In some implementations, the data may relate to a value received and/or expended by the benefit manager organization (e.g., related to providing a service to a customer). Additionally, or alternatively, the data may relate to a manner in which the organization has implemented the process. For example, the data may include data elements that identify a quantity of people associated with performance of a process, departments and/or functional areas of the benefit manager organization related to the process, computing, processing, and/or memory resources associated with implementation of the process, and/or the like.

Additionally, or alternatively, the data may relate to a manner in which a customer interacts with the benefit manager organization. For example, the data may relate to types of interactions, quantity of interactions, and/or the like. As another example, the data may relate to the systems with which the customer interacts when interacting with the benefit manager organization, such as a quantity and/or type of systems with which the customer interacts, processing and/or computing resources that the systems consume during a customer interaction, and/or the like. Additionally, or alternatively, and as another example, the data may relate to a manner in which a customer call is handled (e.g., by a customer support center), a manner in which error tickets generated during a customer interaction are handled, and/or the like.

Additionally, or alternatively, the data may relate to metrics associated with the process and/or the operations of the benefit manager organization. For example, the metrics may include a quantity of customers serviced by the benefit manager organization, a quantity and/or types of services provided to a customer, medical information related to a customer, errors related to processing customer information, an amount of time, processing resources, and/or computing resources used to implement a process and/or perform operations of the benefit manager organization, and/or the like.

In some implementations, the data may include text (e.g., text from patient medication records, prescriptions, receipts, customer surveys, etc.), audio data, and/or video data. In some implementations, recommendation platform 230 may receive the data in a file. For example, recommendation platform 230 may receive the data in a comma separated values (CSV) file, a spreadsheet file, a text file, and/or the like. In this way, recommendation platform 230 may receive various types of files. In some implementations, recommendation platform 230 may receive millions, billions, or trillions of data elements when receiving the data.

In some implementations, recommendation platform 230 may store the data. For example, recommendation platform 230 may store the data using memory resources associated with recommendation platform 230. In some implementations, when storing the data, recommendation platform 230 may aggregate and/or merge the data with other data, deduplicate the data, and/or identify missing or corrupted data and obtain replacement data (e.g., using information related to the data, querying data from external information source 220, cross-referencing the data to identify the missing or corrupted data, and/or the like). This conserves memory resources of recommendation platform 230 and/or conserves processing resources of recommendation platform 230 by reducing errors in the data, reducing duplicate data, and/or the like. In some implementations, recommendation platform 230 may use a big data tool to aggregate and/or merge the data (e.g., to aggregate and/or merge millions, billions, trillions, etc., of data elements). In this way, recommendation platform 230 may receive a data set that cannot be received and/or processed manually, thereby increasing an efficiency of receiving data related to a benefit manager organization.

In this way, recommendation platform 230 may receive data associated with a performance of a process and/or operations of a benefit manager organization.

As further shown in FIG. 4, process 400 may include processing the data using a technique based on receiving the data (block 420). For example, recommendation platform 230 may process the data using a technique. In some implementations, recommendation platform 230 may process millions, billions, trillions, etc. of data elements when processing the data. In this way, recommendation platform 230 may process a data set that cannot be processed manually.

In some implementations, the technique may include natural language processing, text analysis, computational linguistics, and/or or the like. In some implementations, when processing the data using natural language processing, recommendation platform 230 may process the data to identify a term included in the data. For example, recommendation platform 230 may adjust characters (e.g., add characters, remove characters, etc.), adjust spacing in the data (e.g., add or remove spaces), expand acronyms included in the data (e.g., replace "EPA" with "Environmental Protection Agency"), replace a symbol with a term (e.g., replace an "@" symbol with the term "at"), convert a term included in the data to a root term (e.g., convert "processing," "processed," or "processor" to "process"), and/or the like.

Additionally, or alternatively, the technique may include pattern recognition, trend analysis, and/or the like. For example, recommendation platform 230 may use a big data tool to process millions, billions, or trillions of data elements to identify previously unidentifiable relationships and/or trends among data elements of the data, such as to identify a deficiency related to the data, to identify a manner in which to positively impact a deficiency, and/or the like.

Additionally, or alternatively, the technique may include automatic speech recognition (ASR), computer speech recognition, speech-to-text, and/or the like. For example, recommendation platform 230 may convert audio from an interview or customer support call to text.

In some implementations, recommendation platform 230 may process a file associated with the data. In some implementations, recommendation platform 230 may process multiple file types. This improves performance of recommendation platform 230 by permitting recommendation platform 230 to process files of various types (e.g., relative to processing a single type of file). In some implementations, recommendation platform 230 may process the data to identify metadata associated with the data (e.g., an identifier associated with the data that identifies a process with which the data is associated, a timestamp associated with the data, etc.). For example, recommendation platform 230 may process the data to identify a process with which the data is associated, a functional area of the benefit manager organization with which the data is associated, operations of the benefit manager organization with which the data is associated, and/or the like. This permits recommendation platform 230 to quickly and efficiently identify metadata associated with the data, thereby conserving processing resources of recommendation platform 230.

In some implementations, recommendation platform 230 may process the data to permit analysis of the data. For example, by processing the data, recommendation platform 230 may reduce errors associated with the data, may format the data such that recommendation platform 230 can map the data to an operating model (as described below), may normalize the data to permit inter-organization comparisons, and/or the like. This conserves processing resources of recommendation platform 230 and improves analyses using the data relative to using unprocessed data.

In this way, recommendation platform 230 may process the data using a technique based on receiving the data.

As further shown in FIG. 4, process 400 may include mapping the data to a benefit manager operating model based on processing the data (block 430). For example, recommendation platform 230 may map the data to a benefit manager operating model based on processing the data. In some implementations, a benefit manager operating model may include a model that identifies an area (e.g., a functional area and/or a sub-area of a functional area of a benefit manager organization that the benefit manager organization uses to implement a process and/or operations).

In some implementations, the benefit manager operating model may be based on analyses of other organizations. For example, the benefit manager operating model may represent a benchmark structure and/or an organizational structure of another benefit manager organization (e.g., a benefit manager organization identified as a high-performing benefit manager organization), an industry standard, and/or the like. In some implementations, recommendation platform 230 may use the operating model to identify a rule (e.g., related to data, a functional area, or a sub-area), a threshold related to data, an industry standard, a metric related to a process and/or operations of a benefit manager organization, and/or the like to apply to data related to a process and/or operations of a benefit manager organization when analyzing the data. This permits recommendation platform 230 to quickly identify a rule, a threshold, a metric, and/or the like by mapping data to a benefit manager operating model.

In some implementations, the benefit manager operating model may be based on a type of benefit manager organization being analyzed. For example, recommendation platform 230 may use a PBM operating model for a PBM organization type, may use a specialty PBM operating model for a specialty PBM organization type, may use a manufacturing operating model for a manufacturing organization, and/or the like.

Additionally, or alternatively, the benefit manager operating model may be based on a type of analysis being performed. For example, the benefit manager operating model may include functional areas of a benefit manager organization with which a customer may interact when analyzing customer interactions with the benefit manager organization. As another example, recommendation platform 230 may use an operating model that identifies functional and/or sub-areas of a benefit manager organization that may be associated with implementation of a process when analyzing a process of the benefit manager organization. As another example, recommendation platform 230 may use an operating model that identifies infrastructure (e.g., call centers, departments, systems, etc.) of a benefit manager organization when analyzing infrastructure of the benefit manager organization. As another example, recommendation platform 230 may use an operating model for a manufacturing organization when analyzing a manufacturing organization.

In some implementations, recommendation platform 230 may map the data to an area of the benefit manager operating model. In some implementations, recommendation platform 230 may map the data based on an identifier associated with the data (e.g., an identifier that identifies a functional area with which the data is associated). This conserves processing resources of recommendation platform 230 via quick and efficient mapping of the data.

Additionally, or alternatively, recommendation platform 230 may map the data based on a type of the data (e.g., when the functional areas of the benefit manager organization do not match the functional areas of the benefit manager operating model). For example, recommendation platform 230 may map the data based on previous mappings, using artificial intelligence, and/or the like. This improves mapping of the data by permitting recommendation platform 230 to map data when functional areas of the benefit manager organization being analyzed do not match functional areas of the benefit manager operating model (e.g., relative to a device that cannot map data when functional areas or sub-areas of a benefit manager organization do not match functional areas or sub-areas of a benefit manager operating model).

In some implementations, recommendation platform 230 may map the data to permit analysis of the data. For example, recommendation platform 230 may map the data to permit a comparison of a process implemented by the benefit manager organization and another benefit manager organization identified as a high performing benefit manager organization, to identify a deficiency related to a process and/or operations of the benefit manager organization, and/or the like, as described in more detail elsewhere herein.

In some implementations, recommendation platform 230 may generate the benefit manager operating model prior to mapping the data. For example, recommendation platform 230 may receive data associated with other benefit manager organizations, such as a PBM organization, a specialty PBM organization, and/or the like. Continuing with the example, recommendation platform 230 may receive data associated with multiple benefit manager organizations that are different than the benefit manager organization being analyzed.

In some implementations, recommendation platform 230 may use metadata associated with the data to identify the type of benefit manager organization. For example, recommendation platform 230 may group the data based on type and may analyze the data to identify trends in the data (e.g., functional areas or sub-areas common to a threshold quantity or percentage of the benefit manager organizations). In some implementations, recommendation platform 230 may generate the operating model based on analyzing the data. For example, recommendation platform 230 may generate an operating model for each type of benefit manager organization identified. As a particular example, recommendation platform 230 may generate a PBM operating model to be used to analyze a PBM organization, a specialty PBM operating organization to be used to analyze a specialty PBM organization, and/or the like.

In some implementations, recommendation platform 230 may use cross-domain data to generate the benefit manager operating model. For example, when recommendation platform 230 lacks a threshold amount of data for specialty PBM organizations to generate a specialty PBM operating model, recommendation platform 230 may identify similar benefit manager organizations (e.g., PBM organizations), and may use related data to generate the specialty PBM operating model. In this way, recommendation platform 230 may generate a benefit manager operating model.

In this way, recommendation platform 230 may map the data to a benefit manager operating model based on processing the data.

As further shown in FIG. 4, process 400 may include performing an analysis of the data based on mapping the data to the benefit manager operating model (block 440). For example, recommendation platform 230 may perform an analysis of the data based on mapping the data to the benefit manager operating model.

In some implementations, recommendation platform 230 may use a metric, a rule, data related to a process and/or operations of another benefit manager organization (e.g., a high performing benefit manager organization), and/or the like identified by a benefit manager operating model to perform the analysis. For example, when recommendation platform 230 maps data to the benefit manager operating model, recommendation platform 230 may identify a metric, a rule, other data, and/or the like associated with a functional area and/or a sub-area of the benefit manager operating model to which the data was mapped. Continuing with the previous example, recommendation platform 230 may use the identified metric, rule, data, and/or the like to perform the analysis. In some implementations, recommendation platform 230 may perform an analysis to identify a deficiency related to a process implemented by a benefit manager organization and/or a manner in which to improve operations of the benefit manager organization.

In some implementations, recommendation platform 230 may identify a deficiency when a metric does not satisfy a threshold, satisfies a first threshold rather than a second threshold, fails to satisfy a threshold by a threshold amount, and/or the like. Additionally, or alternatively, recommendation platform 230 may compare functional areas of a benefit manager organization and a benefit manager operating model and may identify a deficiency when the benefit manager organization is missing a functional area or a sub-area. Additionally, or alternatively, recommendation platform 230 may identify a deficiency related to customer interactions (e.g., when a customer interacts with a threshold quantity of functional areas or systems of the benefit manager organization).

Additionally, or alternatively, recommendation platform 230 may identify a deficiency related to a process of the benefit manager organization. For example, recommendation platform 230 may identify that the benefit manager organization uses a threshold quantity of functional areas to implement a process, that the functional areas used to implement the process are different from another benefit manager organization (or industry standard), and/or the like.

Additionally, or alternatively, recommendation platform 230 may identify a deficiency related to infrastructure of the benefit manager organization. For example, recommendation platform 230 may identify that the benefit manager organization has redundant infrastructure (e.g., multiple call centers that respond to the same issues, multiple of the same departments, multiple claims multiple processing centers, etc.), a threshold quantity of infrastructure (e.g., a threshold quantity of call centers, a threshold quantity of departments, a threshold quantity of claims processing centers, etc.), that infrastructure of the benefit manager organization is different from another benefit manager organization (e.g., different types and/or quantities of infrastructure), and/or the like. Additionally, or alternatively, recommendation platform 230 may identify similar deficiencies for a manufacturing organization, an information technology organization, and/or the like.

In some implementations, recommendation platform 230 may identify a deficiency and/or a manner in which to improve a benefit manager organization by comparing functional areas of the benefit manager organization that are used to implement a process and functional areas of another benefit manager organization and determine that the functional areas used are different. In this case, recommendation platform 230 may identify a deficiency and/or a manner in which to improve the operations of a benefit manager organization by identifying functional areas that the benefit manager organization can use to implement a process and that are different than the functional areas that the benefit manager organization is using.

Additionally, or alternatively, recommendation platform 230 may identify a deficiency and/or a manner in which to improve an organization by identifying a potentially inefficient combination of functional areas or sub-areas used to implement a process (e.g., based on previous analyses that identified an inefficient combination of functional areas, identified using machine learning, identified using pattern recognition, and/or the like). In this case, recommendation platform 230 may identify a deficiency and/or a manner in which to improve operations of the benefit manager organization by identifying a more efficient combination of functional areas and/or sub-areas to use to implement a process and/or operations, thereby conserving processing resources related to implementing the process and/or operations. In this way, recommendation platform 230 may identify a deficiency and/or a manner in which to improve a process and/or operations of the benefit manager organization by identifying a more efficiency combination of functional areas and/or sub-areas to use to implement a process and/or operations.

Additionally, or alternatively, recommendation platform 230 may identify a deficiency and/or a manner in which to improve a benefit manager organization by identifying a threshold quantity of functional areas or sub-areas that the benefit manager organization uses to implement the process and/or operations. For example, the threshold quantity may indicate a complex implementation of a process and/or operations, thereby reducing efficiency of the operations of the benefit manager organization.

Additionally, or alternatively, recommendation platform 230 may identify a deficiency and/or manner in which to improve the benefit manager organization by identifying a missing functional area or sub-area, and may identify a process or operational element (e.g., a department, a group, etc. within the benefit manager organization) that supplies a function associated with the missing functional area or sub-area. Additionally, or alternatively, recommendation platform 230 may identify a deficiency and/or a manner in which to improve a benefit manager organization by identifying a redundant process or operational element (e.g., call center, claim processing department, etc.), and may determine to eliminate the redundant process or operational element to improve the benefit manager organization.

Additionally, or alternatively, recommendation platform 230 may identify a particular hardware resources (e.g., computer hardware, electronic devices, etc.) needed to perform a process and/or operations, and/or may identify a volume or capacity of the hardware resources (e.g., memory, processing, etc.) needed, and may determine whether the hardware resources satisfy a threshold, satisfy a first threshold but not a second threshold and/or the like. For example, recommendation platform 230 may compare computing resources and/or processing resources of a device that the benefit manager organization uses to implement a process and/or operations and the computing resources and/or processing resources of a device of another benefit manager organization, a threshold, and/or the like, and identify a deficiency based on the comparison.

In this way, recommendation platform 230 may identify a deficiency and/or a manner in which to improve a process and/or operations of a benefit manager organization based on hardware resources associated with the benefit manager organization. This conserves processing resources related to implementation of a process and/or operations, improves an efficiency of a process and/or operations, and/or the like via optimization of hardware resources.

In some implementations, recommendation platform 230 may generate a score related to an identified deficiency. For example, the score may relate to a severity of an inefficiency, resources and/or expenses associated with fixing an identified deficiency or with improving operations, a priority of the deficiency (e.g., for fixing the deficiency), a priority of improving the operations, and/or the like. In some implementations, recommendation platform 230 may generate the score using information from previous analyses that indicates a severity of a deficiency, information that indicates a difficulty of fixing the deficiency, information input by a user of client device 210 that indicates a priority for fixing the deficiency and/or a severity of the deficiency, and/or the like. In this way, recommendation platform 230 may quickly and efficiently prioritize deficiencies and determine a severity of a first deficiency relative to a second deficiency.

In some implementations, recommendation platform 230 may store a result of the analysis in a knowledge base or knowledge graph. For example, recommendation platform 230 may aggregate the data with information for results of other analyses. In some implementations, recommendation platform 230 may use the knowledge base to perform machine learning to improve future analyses of the same or a different benefit manager organization, to perform a big data analysis, and/or the like. In some implementations, a knowledge base or knowledge graph may include technology used to store complex structured and unstructured data used by a computer system.

In this way, recommendation platform 230 may perform an analysis of data based on mapping the data to a benefit manager operating model.

As further shown in FIG. 4, process 400 may include performing an action to positively impact the performance of the process and/or the operations of the benefit manager organization based on performing the analysis (block 450). For example, recommendation platform 230 may perform an action to positively impact the performance of the process and/or the operations of the benefit manager organization based on performing the analysis. In some implementations, a positive impact may occur when an action causes a desired result or action to be achieved. Additionally, or alternatively, a positive impact may occur when an action increases the likelihood that a desired result of an action will be achieved.

In some implementations, recommendation platform 230 may generate a recommendation. For example, recommendation platform 230 may generate a recommendation to use different functional areas to implement a process and/or operations, a recommendation to use different systems to implement a process and/or operations (e.g., to consolidate systems), a recommendation to use different sub-areas to implement a process and/or operations in a functional area, a recommendation to add a process and/or operations associated with a functional area or sub-area, a recommendation to remove a process and/or operations associated with a functional area or sub-area, and/or the like.

In some implementations, recommendation platform 230 may generate the recommendation using information related to the analysis. For example, recommendation platform 230 may generate a recommendation to fix a particular deficiency identified during an analysis. In some implementations, recommendation platform 230 may generate multiple recommendations. In some implementations, recommendation platform 230 may generate a score for each of the multiple recommendations. For example, recommendation platform 230 may generate a score based on a predicted impact of the recommendation (e.g., as determined using data from prior analyses and prior implemented recommendations).

In some implementations, recommendation platform 230 may provide information identifying a recommendation to a device to cause the device to implement the recommendation based on a score for the recommendation. For example, recommendation platform 230 may provide information identifying a recommendation that has the highest score relative to other scores for other recommendations, that has a threshold score, and/or the like.

Additionally, or alternatively, recommendation platform 230 may perform another action based on the score for the recommendation. For example, recommendation platform 230 may perform an action to implement a recommendation when the score satisfies a threshold, perform a different action when the score fails to satisfy a threshold, and/or the like. In this way, recommendation platform 230 may optimize providing recommendations to a device that implements a process and/or operations of a benefit management organization, thereby increasing an efficiency of providing recommendations and/or conserving processing resources of recommendation platform 230 (e.g., relative to providing all recommendations, providing a recommendation that may fail to have a predicted result, etc.).

In some implementations, recommendation platform 230 may send a message (e.g., an email or a short message service (SMS) message) to client device 210. For example, the message may include information related to the analysis and/or a generated recommendation. In some implementations, recommendation platform 230 may schedule a meeting (e.g., to discuss the analysis or a generated recommendation). For example, recommendation platform 230 may schedule a meeting using electronic calendars of individuals associated with the benefit manager organization to identify an available time for the meeting.

In some implementations, recommendation platform 230 may send a set of instructions to modify a manner in which devices implement a process and/or operations. For example, recommendation platform 230 may send a set of instructions to modify which systems and/or devices are used to implement a process (e.g., to reduce or increase a quantity of systems used). In this way, recommendation platform 230 may modify a manner in which a system and/or device implements a process and/or operations.

In some implementations, recommendation platform 230 may manage implementation of a process and/or operations. For example, recommendation platform 230 may track metrics associated with implementation of a process and/or operations, may perform an analysis (e.g., of the metrics) to determine a more efficient manner of performing the process and/or operations, and/or the like. In this case, recommendation platform 230 may send a set of instructions (e.g., to client device 210) when recommendation platform 230 identifies a more efficient manner for implementing the process and/or operations.

In some implementations, recommendation platform 230 may provide information for an analysis to another recommendation platform 230. For example, recommendation platform 230 may provide the information to improve future analyses of the other recommendation platform 230. In this way, recommendation platform 230 improves an accuracy of an analysis of the other recommendation platform 230, thereby conserving processing resources that would otherwise be consumed due to an inaccurate or inefficient analysis.

In some implementations, recommendation platform 230 may monitor post-recommendation actions, such as to determine whether an impact of an action matches a predicted impact. For example, if recommendation platform 230 generates a recommendation to reduce a quantity of devices used to implement a process, recommendation platform 230 may monitor the process to determine whether the devices that are implementing the process use fewer processing resources after the quantity of devices is reduced. This improves implementation of a recommendation by preventing a device from implementing an ineffective recommendation.

In some implementations, recommendation platform 230 may bring a device and/or software online or offline. For example, recommendation platform 230 may send a set of instructions to a device, install and/or activate software on a device, and/or the like. Additionally, or alternatively, recommendation platform 230 may update software installed on a device. Additionally, or alternatively, recommendation platform 230 may push software to a device, so as to update the software. In this way, recommendation platform 230 may improve functioning of a device via updating of software, adjusting whether the device is online or offline, and/or the like.

In some implementations, recommendation platform 230 may perform the actions described herein in real-time or near real-time. For example, recommendation platform 230 may analyze and modify a process and/or operations of a benefit manager organization as the benefit manager organization is implementing the process and/or the operations. This conserves processing resources of a device used to implement the process and/or operations by reducing an amount of time that the device implements a process and/or operations that include a deficiency (e.g., relative to delayed performance of an action).

In this way, recommendation platform 230 may perform an action to positively impact a performance of a process and/or operations of a benefit manager organization based on performing an analysis.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5A-5D are diagrams of an example implementation 500 relating to example process 400 shown in FIG. 4. FIGS. 5A-5D show an example of tracking customer interactions with a PBM and/or specialty PBM organization for a particular process. For example, recommendation platform 230 may track the functional areas, sub-areas, and/or corresponding systems to identify a manner in which a customer interacts with the PBM and/or specialty PBM organization. As shown in FIGS. 5A-5D, example implementation 500 may include client devices 210, external information sources 220, and recommendation platform 230.

As shown in FIG. 5A, and by reference number 505, recommendation platform 230 may receive data related to an interaction of an individual with a PBM and/or specialty PBM organization (e.g., customer interaction data). For example, as shown by reference number 510, the customer interaction data may include data elements associated with customer and functional-area interactions, a quantity of interactions, types of interactions, and/or the like. As shown by reference number 515, recommendation platform 230 may process the data using one or more techniques (e.g., natural language processing, text analysis, computational linguistics, etc.), as described elsewhere herein.

Figure 5B:
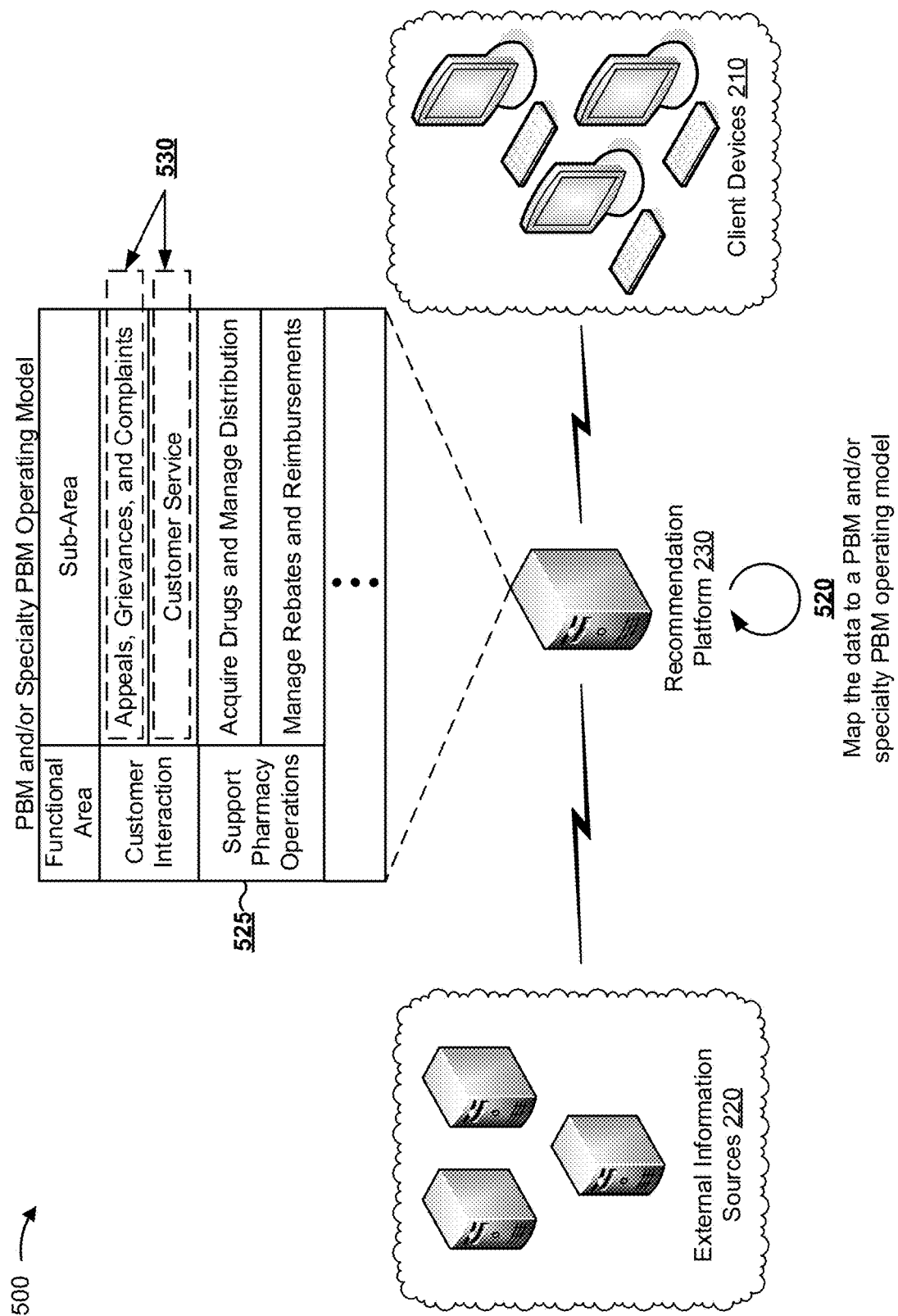

As shown in FIG. 5B, and by reference number 520, recommendation platform 230 may map the data to a PBM and/or specialty PBM operating model. For example, as shown by reference number 525, the PBM and/or specialty PBM operating model may include functional areas (e.g., customer interaction, and support pharmacy operations) and each functional area may be associated with sub-areas. For example, the customer interaction functional area may be associated with appeals, grievances, and complaints and customer service sub-areas, and the support pharmacy operations functional area may be associated with the acquire drugs and manage distribution sub-area and with the manage rebates and reimbursements sub-area.

As shown by reference number 530, recommendation platform 230 may map the data to sub-areas with which a customer interacts (e.g., appeals, grievances, and complaints, and customer service sub-areas). For example, the data may map to a process that the benefit manager organization uses to process a customer complaint and/or provide customer service to a customer. In this way, recommendation platform 230 may determine a manner in which a customer interacts with a benefit manager organization.

Figure 5C:
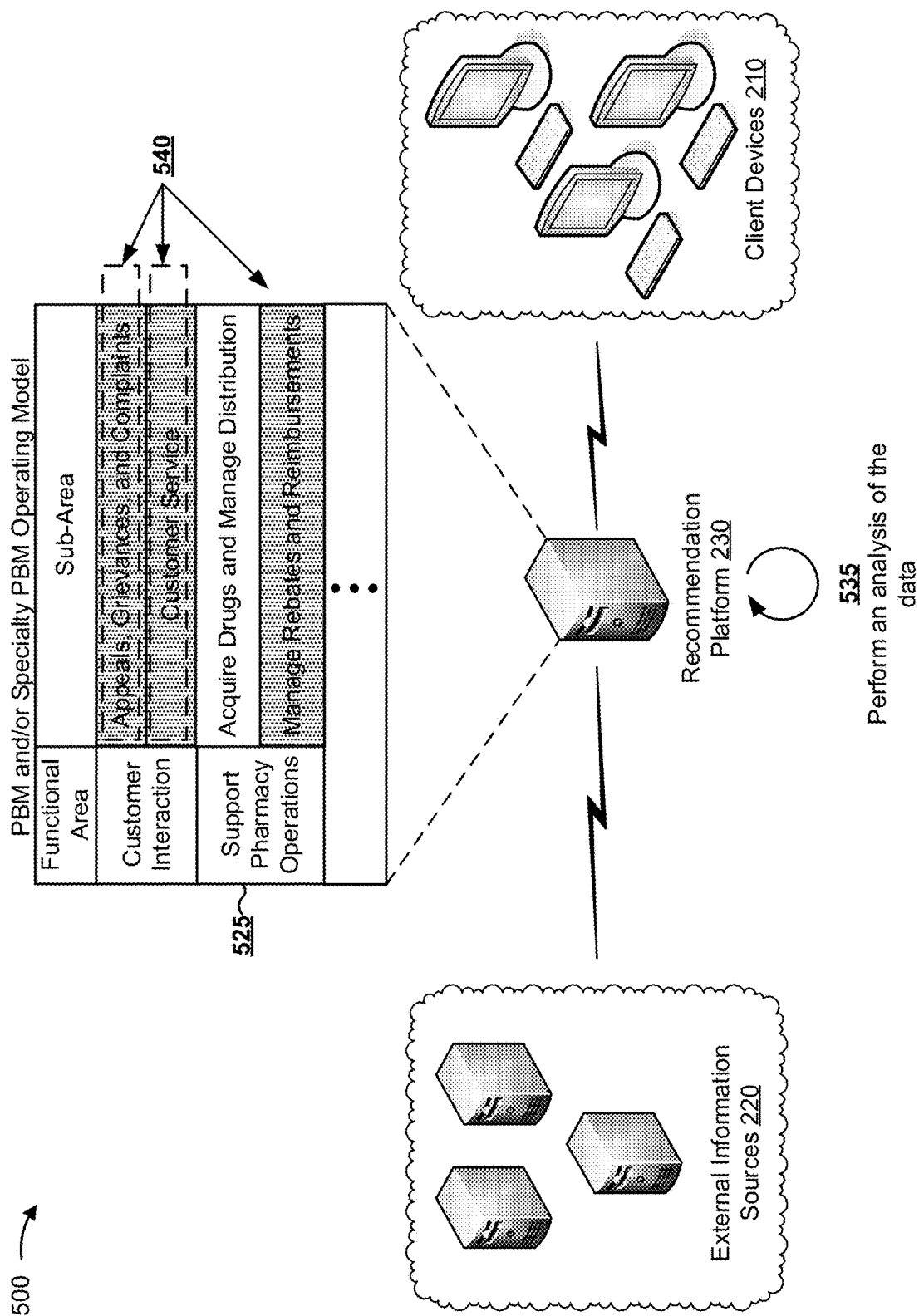

As shown in FIG. 5C, and by reference number 535, recommendation platform 230 may perform an analysis of the data. For example, recommendation platform 230 may determine whether a customer interacts with a threshold quantity of functional areas and/or sub-areas (or corresponding systems), whether a customer interacts with the same functional areas and/or sub-areas as a customer interacting with a different PBM and/or specialty PBM organization, and/or the like.

As shown by reference number 540, recommendation platform 230 may identify sub-areas of another PBM and/or specialty PBM organization (e.g., a model PBM and/or specialty PBM organization) with which a customer interacts, as indicated by lightly shaded boxes, and may compare the sub-areas of the model PBM and/or specialty PBM organization to the sub-areas of the PBM and/or specialty PBM organization being analyzed. In this case, recommendation platform 230 may determine that the PBM and/or specialty PBM organization is not using a manage rebates and reimbursements sub-area to implement a process and that the PBM and/or specialty PBM organization can increase an efficiency of the process by including use of the manage rebates and reimbursements sub-area when implementing the process (e.g., by incorporating functions of the manage rebates and reimbursements sub-area into the process).

Figure 5D:
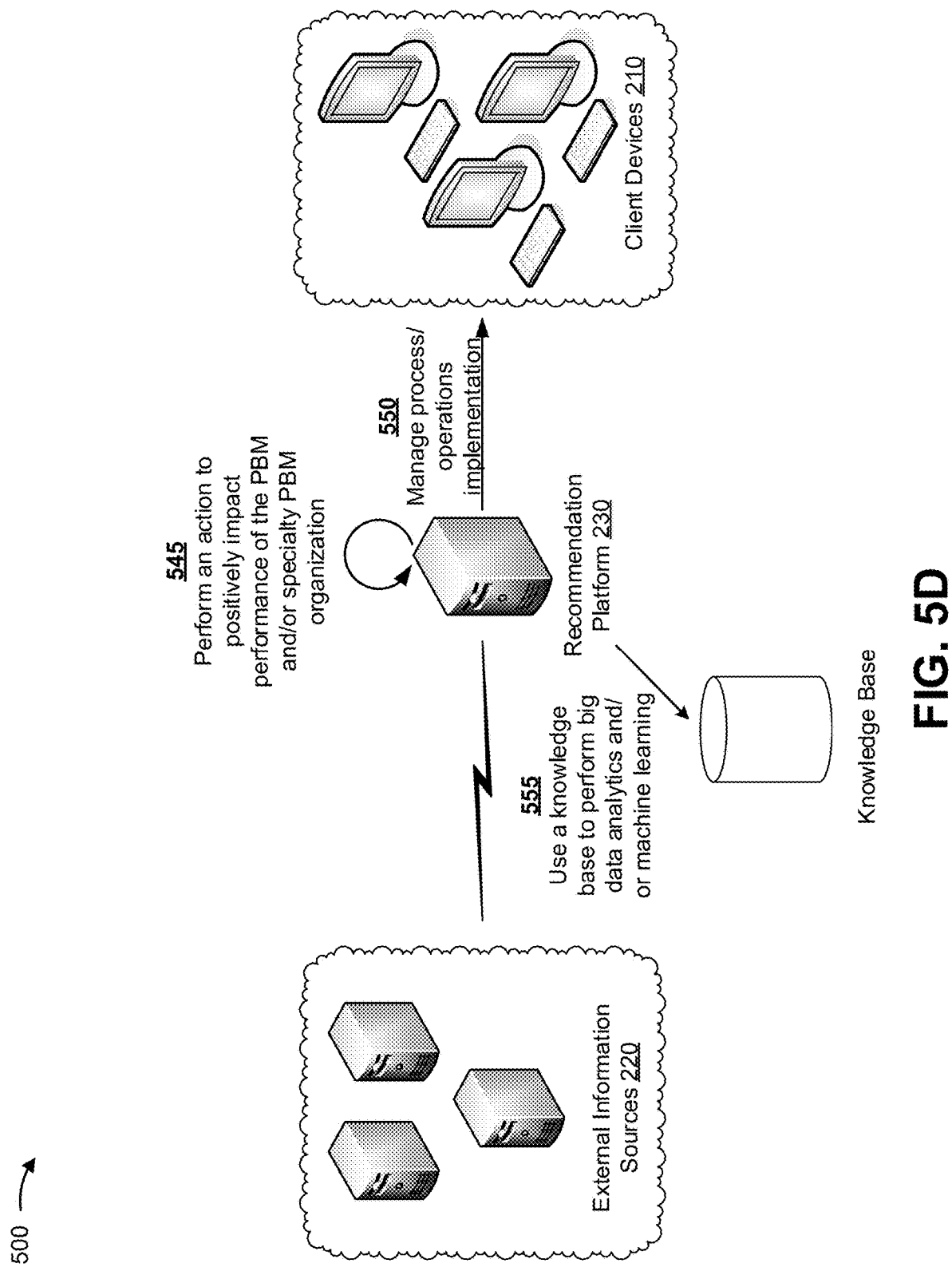

As shown in FIG. 5D, and by reference number 545, recommendation platform 230 may perform an action to positively impact performance of the PBM and/or specialty PBM organization (e.g., generate a recommendation, send a message, schedule a meeting, update software, push software to one or more devices associated with the PBM and/or specialty PBM organization, etc., to improve customer interaction). As shown by reference number 550, recommendation platform 230 may manage implementation of a process and/or operations (e.g., based on the analysis and/or action). As shown by reference number 555, recommendation platform 230 may use a knowledge base to perform big data analytics and/or machine learning using data from performing the analysis, managing process and/or operations implementation, and/or the like.

In some implementations, recommendation platform 230 may perform big data analytics to identify trends among multiple PBM and/or specialty PBM organizations, thereby enabling recommendation platform 230 to identify new and/or different deficiencies. Additionally, or alternatively, recommendation platform 230 may use machine learning to improve an accuracy of identifying a deficiency by using information related to identified deficiencies for multiple PBM and/or specialty PBM organizations.

As indicated above, FIGS. 5A-5D are provided merely as an example. Other examples are possible and may differ from what was described with regard to FIGS. 5A-5D.

FIGS. 6A-6D are diagrams of an example implementation 600 relating to example process 400 shown in FIG. 4. FIGS. 6A-6D show an example of analyzing a combination of functional areas and/or sub-areas that a PBM and/or specialty PBM organization uses to implement a process. As shown in FIGS. 6A-6D, example implementation 600 may include client devices 210, external information sources 220, and recommendation platform 230.

Figure 6A:
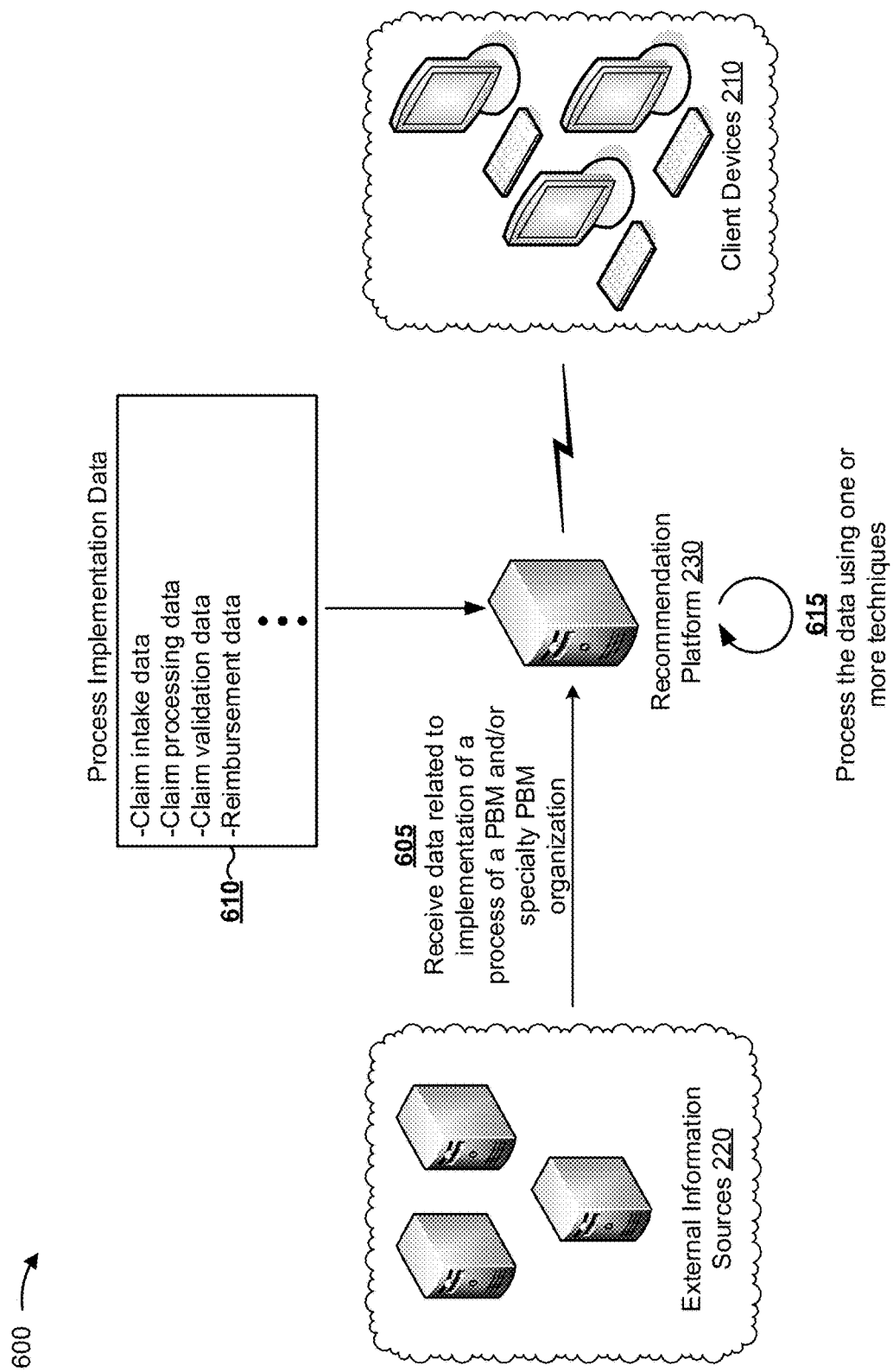
FIGS. 6A-6D are diagrams of an example implementation relating to the example process shown in FIG. 4.

As shown in FIG. 6A, and by reference number 605, recommendation platform 230 may receive data related to implementation of a process of a PBM and/or specialty PBM organization (e.g., process implementation data). For example, and as shown by reference number 610, the process implementation data may include claim intake data, claim processing data, claim validation data, claim reimbursement data, and/or the like. As shown by reference number 615, recommendation platform 230 may process the data using one or more techniques, as described elsewhere herein.

Figure 6B:
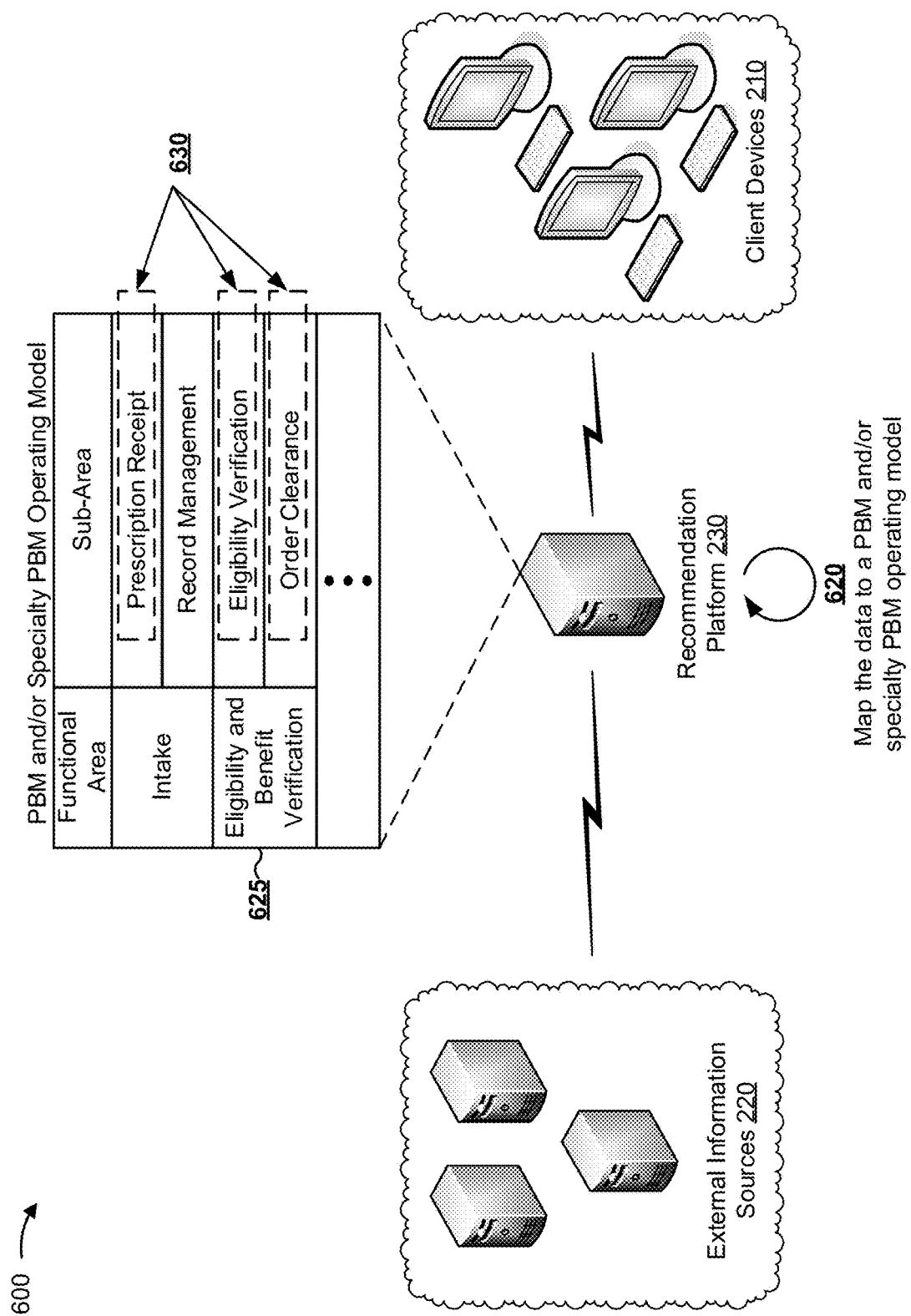

As shown in FIG. 6B, and by reference number 620, recommendation platform 230 may map the data to a PBM and/or specialty PBM operating model. For example, as shown by reference number 625, the PBM and/or specialty PBM operating model may include intake as a functional area that includes prescription receipt and record management as sub-areas, and may include eligibility and benefit verification as a functional area that includes eligibility verification and order clearance as sub-areas. As shown by reference number 630, recommendation platform 230 may map the information to sub-areas that the PBM and/or specialty PBM organization uses to implement a particular process (e.g., prescription receipt, eligibility verification, or order clearance). In some implementations, the mapping of the data may identify a combination of functional areas and/or sub-areas that a PBM and/or specialty PBM uses to implement a process.

Figure 6C:
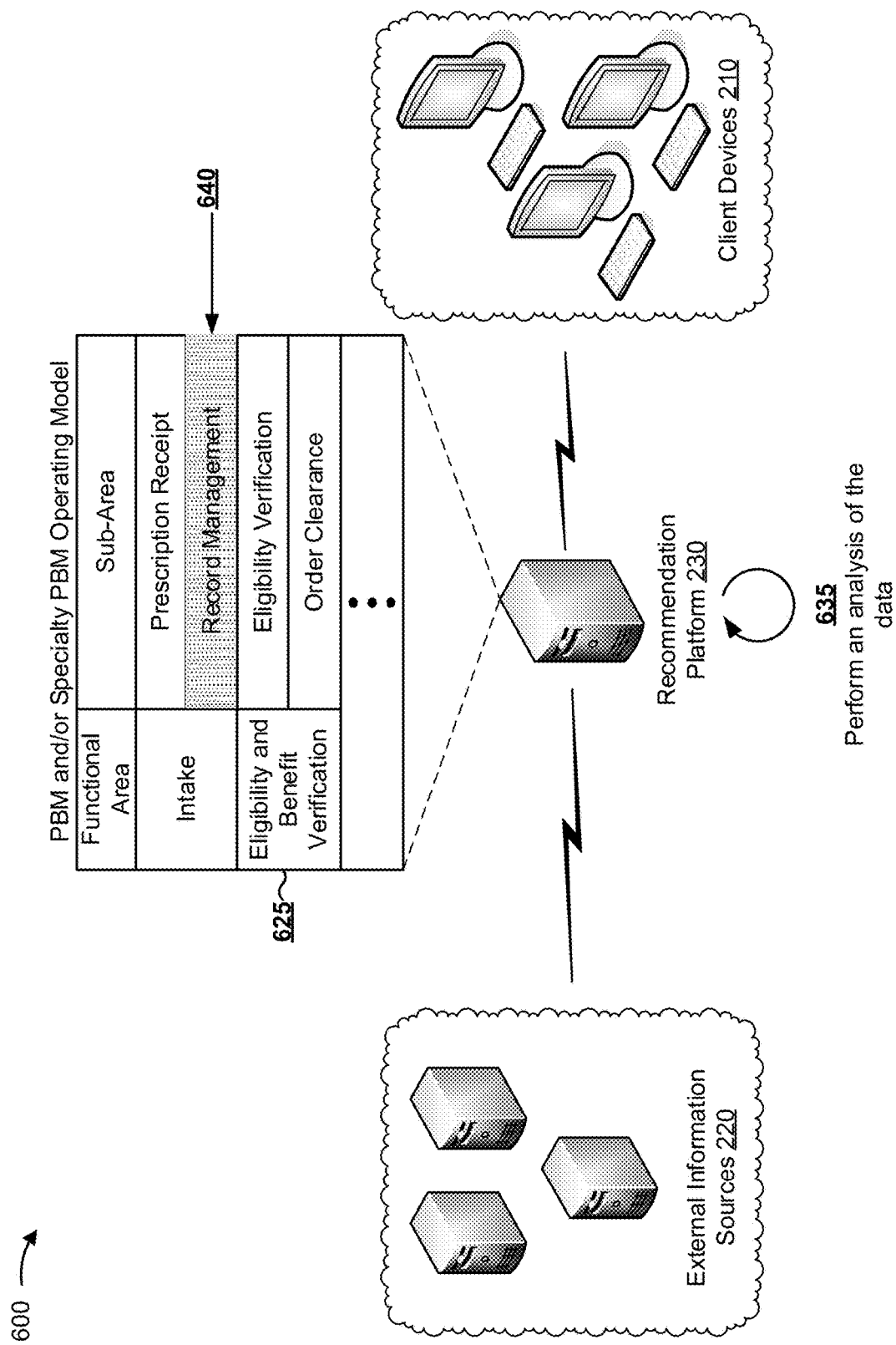

As shown in FIG. 6C, and by reference number 635, recommendation platform 230 may perform an analysis of the data. For example, recommendation platform 230 may analyze sub-areas used to implement the process, such as comparing sub-areas used by a PBM and/or specialty PBM organization and another PBM and/or specialty PBM organization. For example, recommendation platform 230 may determine whether sub-areas used to implement the process are an efficient combination, match an industry standard, and/or the like, based on the comparison. As shown by reference number 640, recommendation platform 230 may identify a sub-area that is missing from implementation of the process (e.g., record management), shown by a lightly shaded rectangle. In this way, recommendation platform 230 may identify a deficiency and/or a manner in which to improve a process and/or operations of a PBM and/or specialty PBM organization.

Figure 6D:
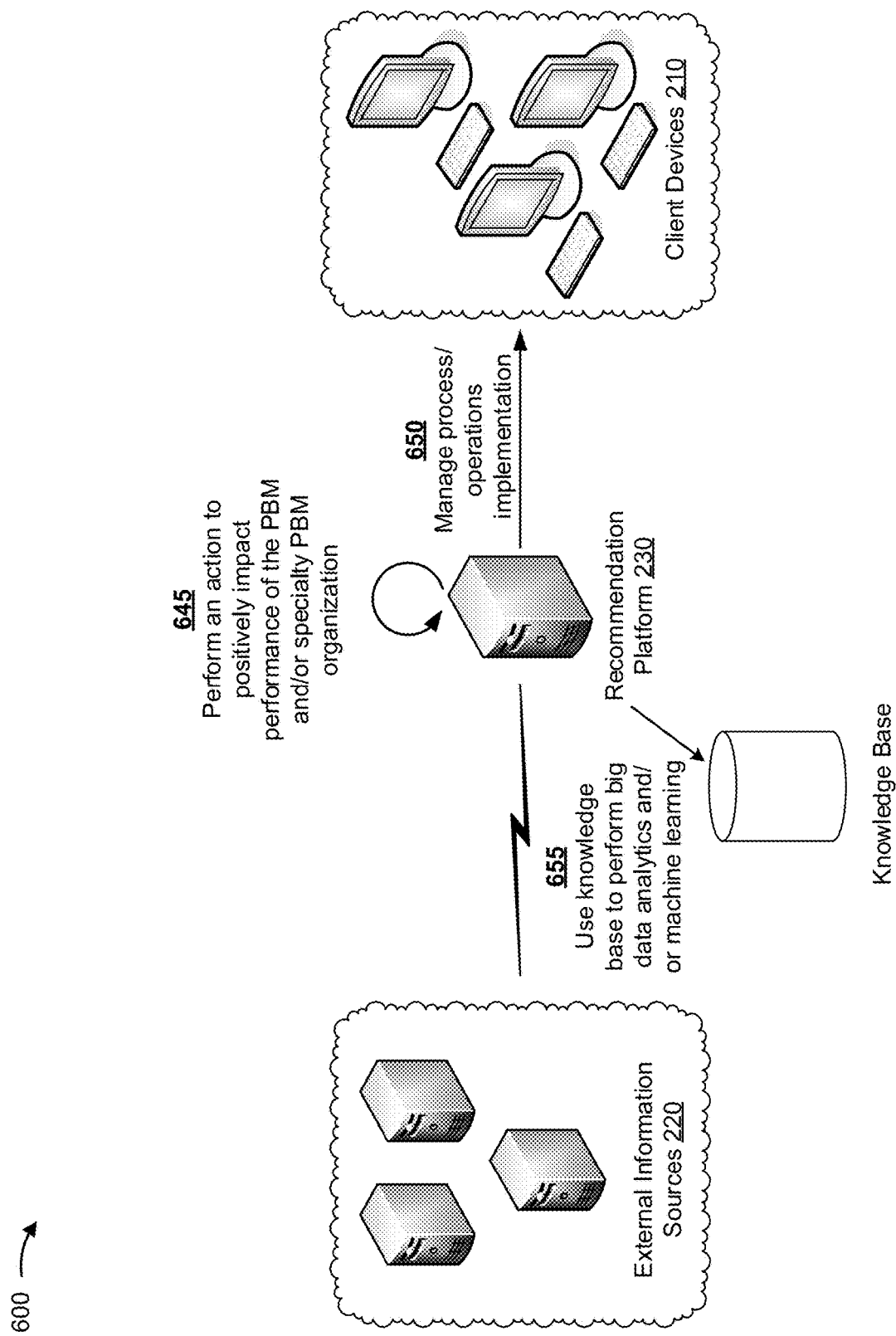

As shown in FIG. 6D, and by reference number 645, recommendation platform 230 may perform an action to positively impact performance of the PBM and/or specialty PBM organization (e.g., generate a recommendation, send a message, schedule a meeting, etc., to improve implementation of a process). As shown by reference number 650, recommendation platform 230 may manage implementation of a process and/or operations (e.g., based on the analysis and/or action). As shown by reference number 655, recommendation platform 230 may use a knowledge base to perform big data analytics and/or machine learning.

As indicated above, FIGS. 6A-6D are provided merely as an example. Other examples are possible and may differ from what was described with regard to FIGS. 6A-6D.

FIGS. 7A-7D are diagrams of an example implementation 700 relating to example process 400 shown in FIG. 4. FIGS. 7A-7D show an example of analyzing a PBM and/or specialty PBM organization's operations and/or infrastructure. As shown in FIGS. 7A-7D, example implementation 700 may include client devices 210, external information sources 220, and recommendation platform 230.

Figure 7A:
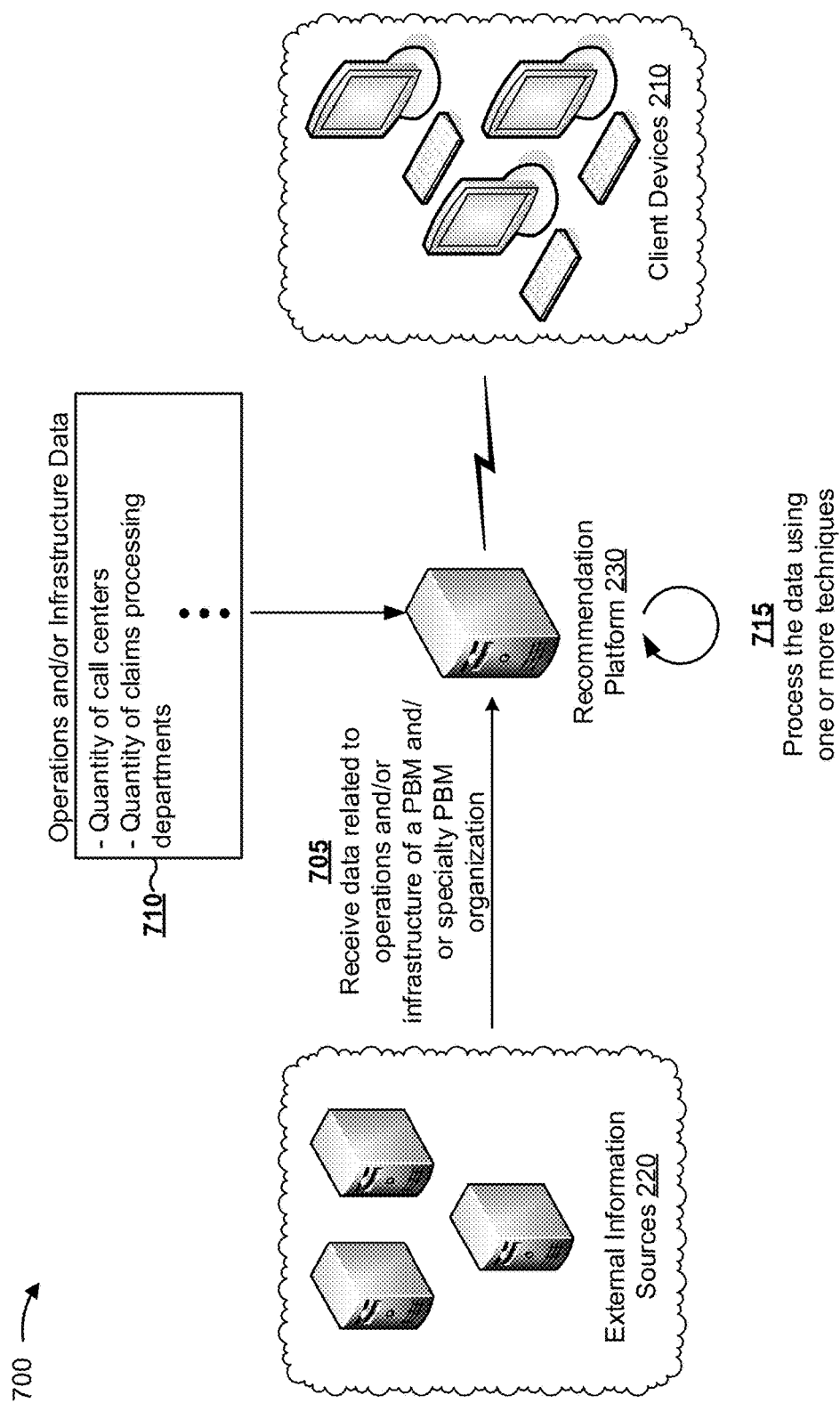
FIGS. 7A-7D are diagrams of an example implementation relating to the example process shown in FIG. 4.

As shown in FIG. 7A, and by reference number 705, recommendation platform 230 may receive data related to operations and/or infrastructure of a PBM and/or specialty PBM organization (e.g., operations and/or infrastructure data). For example, and as shown by reference number 710, the operations and/or infrastructure data may identify a quantity of call centers, a quantity of claims processing departments, and/or the like. As shown by reference number 715, recommendation platform 230 may process the data using one or more techniques, as described elsewhere herein.

Figure 7B:
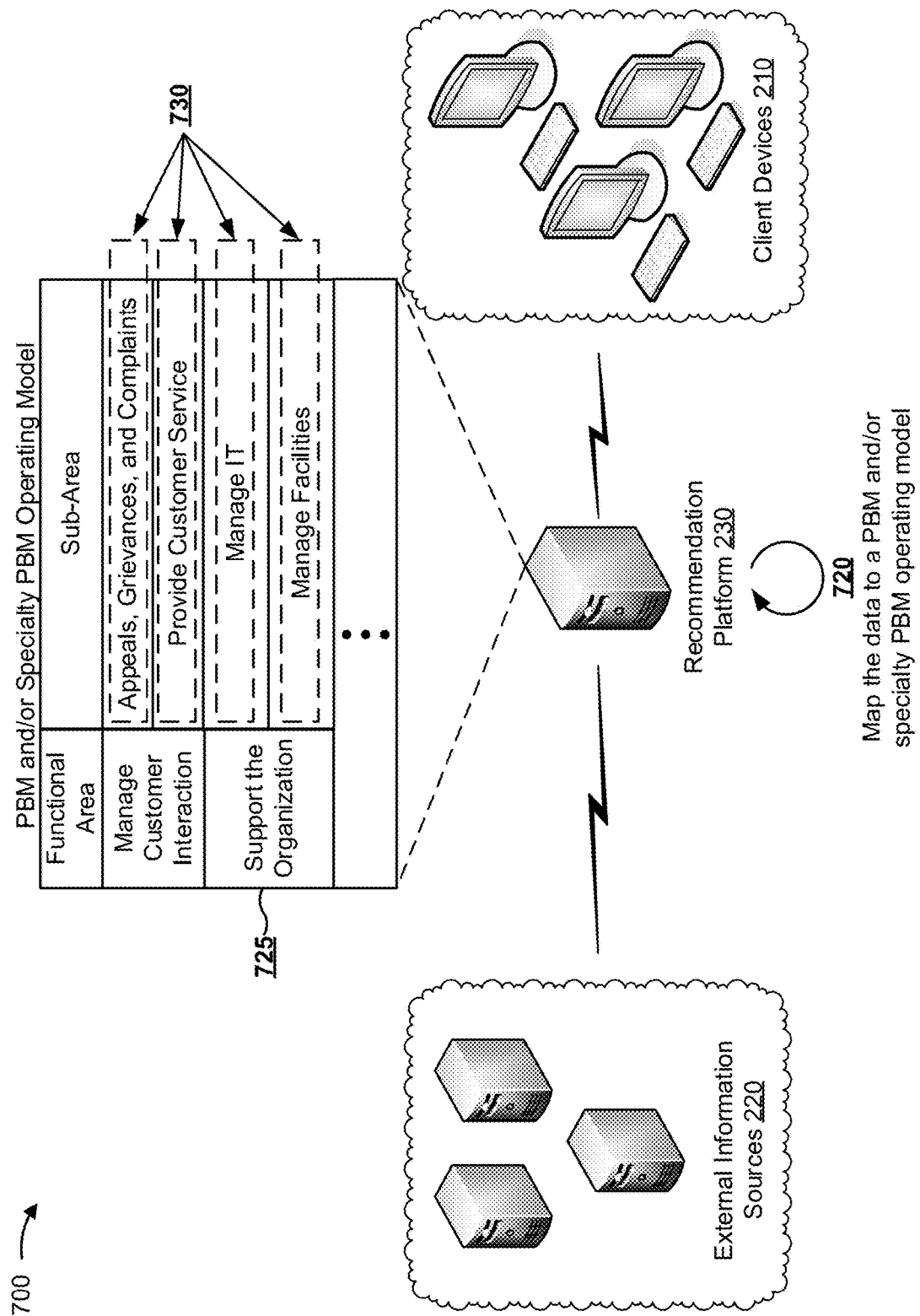

As shown in FIG. 7B, and by reference number 720, recommendation platform 230 may map the data to a PBM and/or specialty PBM operating model. For example, and as shown by reference number 725, the PBM and/or specialty PBM operating model may include manage customer interaction as a functional area that includes appeals, grievances, and complaints and provide customer service as sub-areas, and may include support the organization as a functional area that includes manage information technology (IT) and manage facilities as sub-areas. As shown by reference number 730, recommendation platform 230 may map the data to sub-areas for which data was received (e.g., appeals, grievances, and complaints, provide customer service, manage IT, and manage facilities).

Figure 7C:
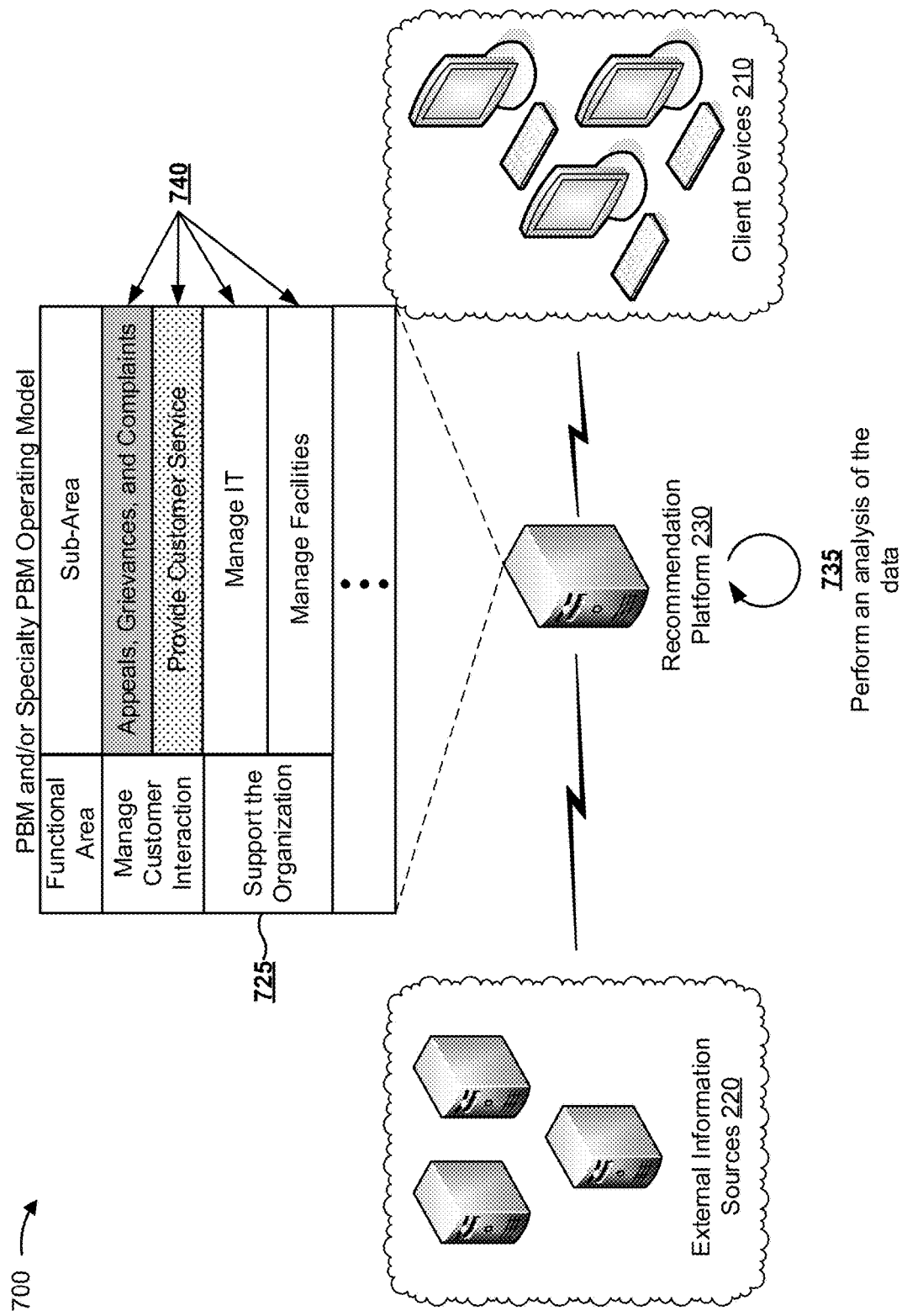

As shown in FIG. 7C, and by reference number 735, recommendation platform 230 may perform an analysis of the data. For example, recommendation platform 230 may determine whether a PBM and/or specialty PBM organization has a deficiency related to operations and/or infrastructure (e.g., have redundant departments, or a lack of departments, associated with a particular functional area or sub-area). As shown by reference number 740, recommendation platform 230 may identify sub-areas (e.g., appeals, grievances, and complaints) with deficient infrastructure (e.g., insufficient infrastructure, or too much infrastructure), shown as a dark shaded rectangle, may identify sub-areas with infrastructure that satisfies a first threshold but not a second threshold (e.g., provide customer service), shown as a lightly shaded rectangle, or sub-areas with a threshold amount of infrastructure (e.g., manage IT and manage facilities), shown as white rectangles. In this way, recommendation platform 230 may identify a deficiency related to operations and/or infrastructure of a PBM and/or specialty PBM organization.

Figure 7D:
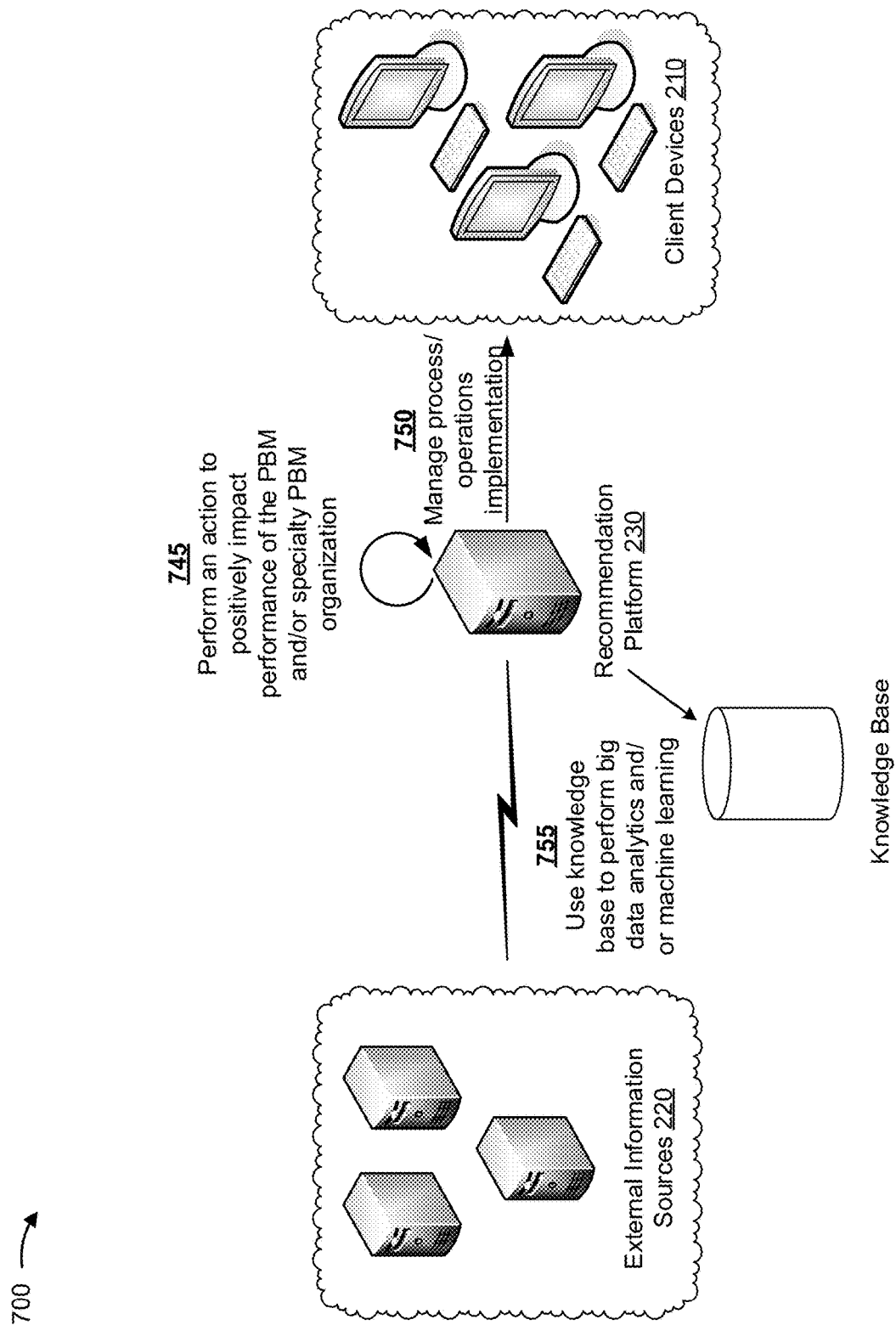

As shown in FIG. 7D, and by reference number 745, recommendation platform 230 may perform an action to positively impact performance of the PBM and/or specialty PBM organization (e.g., generate a recommendation, send a message, schedule a meeting, etc., to improve the organization's operations and/or infrastructure). As shown by reference number 750, recommendation platform 230 may manage implementation of operations and/or infrastructure (e.g., based on the analysis and/or action). As shown by reference number 755, recommendation platform 230 may use a knowledge base to perform big data analytics and/or machine learning using data from the analysis, data from managing implementation of the operations and/or infrastructure, and/or the like.

As indicated above, FIGS. 7A-7D are provided merely as an example. Other examples are possible and may differ from what was described with regard to FIGS. 7A-7D.

FIGS. 8A-8D are diagrams of an example implementation 800 relating to example process 400 shown in FIG. 4. FIGS. 8A-8D show an example of an analysis of a process of a manufacturing organization. As shown in FIGS. 8A-8D, example implementation 800 may include client devices 210, external information sources 220, and recommendation platform 230.

Figure 8A:
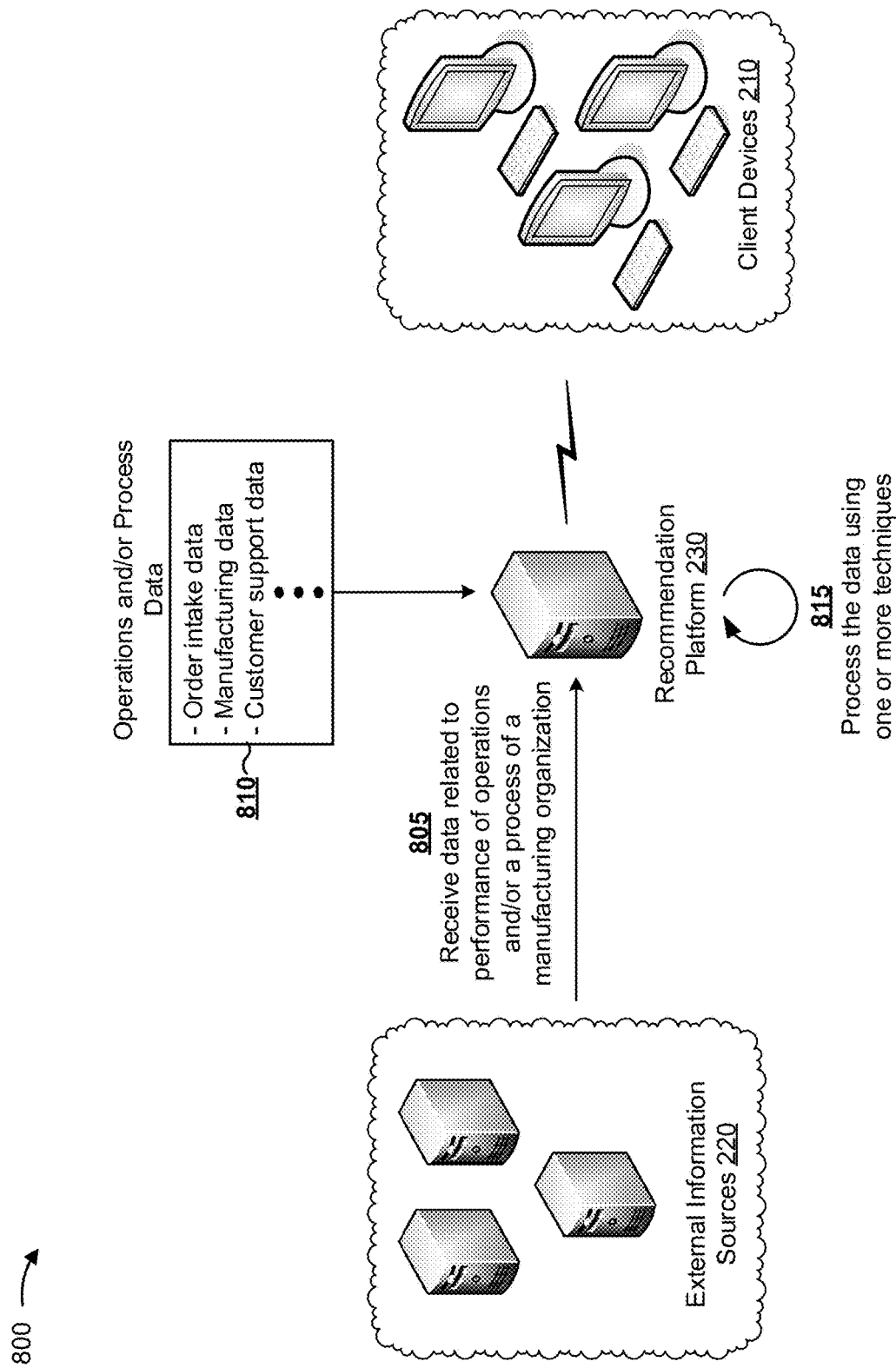
FIGS. 8A-8D are diagrams of an example implementation relating to the example process shown in FIG. 4.

As shown in FIG. 8A, and by reference number 805, recommendation platform 230 may receive data related to performance of operations and/or a process of a manufacturing organization (e.g., operations and/or process data). For example, and as shown by reference number 810, the operations and/or process data may include order intake data, manufacturing data, customer support data, and/or the like. As shown by reference number 815, recommendation platform 230 may process the data using one or more techniques, as described elsewhere herein.

Figure 8B:
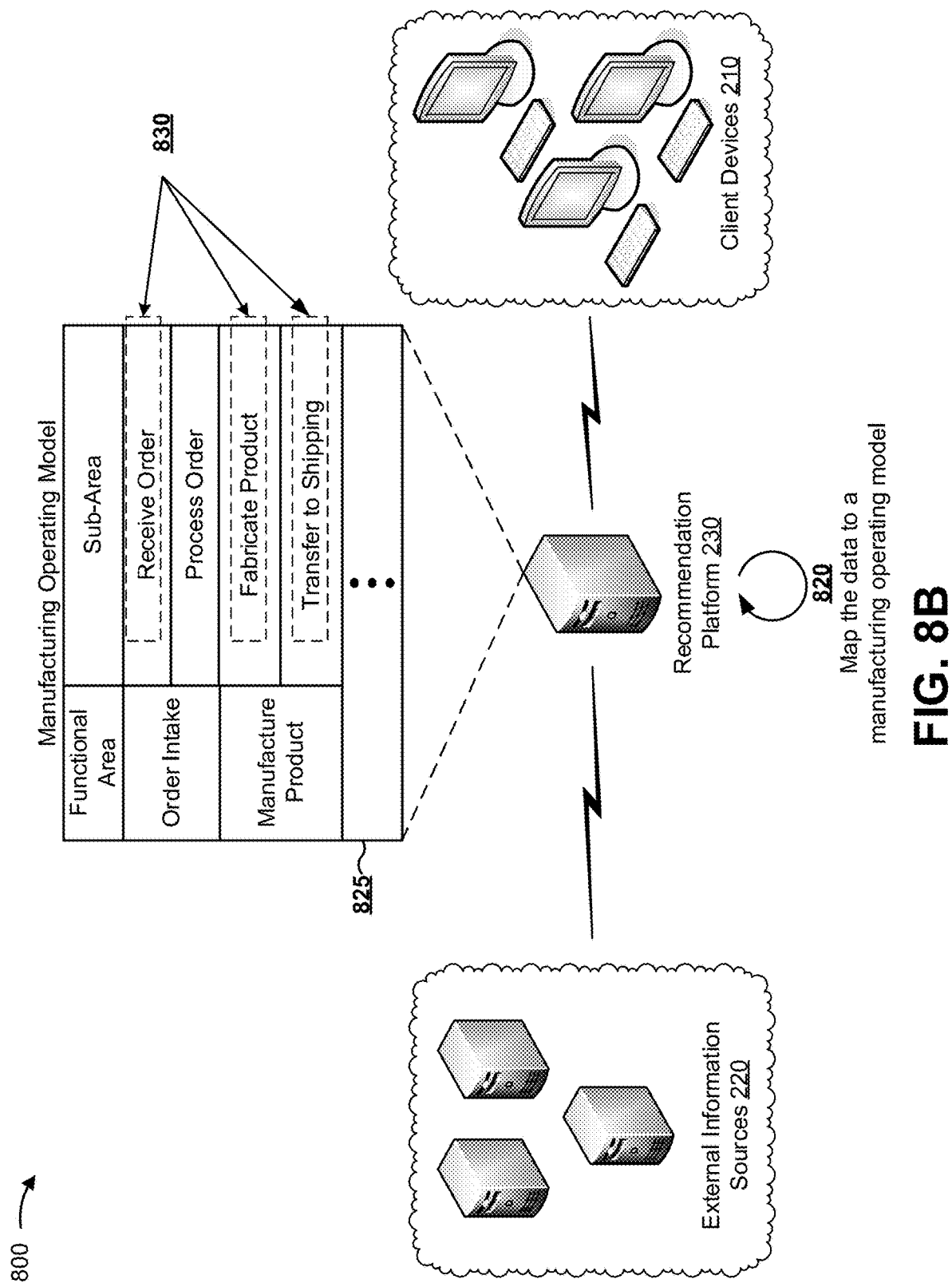

As shown in FIG. 8B, and by reference number 820, recommendation platform 230 may map the data to a manufacturing operating model. For example, and as shown by reference number 825, the manufacturing operating model may include order intake as a functional area that includes receive order and process order as sub-areas, and may include manufacture product as a functional area that includes fabricate product and transfer to shipping as sub-areas. As shown by reference number 830, recommendation platform 230 may identify sub-areas of the manufacturing operating model with which the data is associated (e.g., receive order, fabricate product, and transfer to shipping). In this way, recommendation platform 230 may map data associated with a process and/or operations of a manufacturing organization to a manufacturing operating model.

Figure 8C:
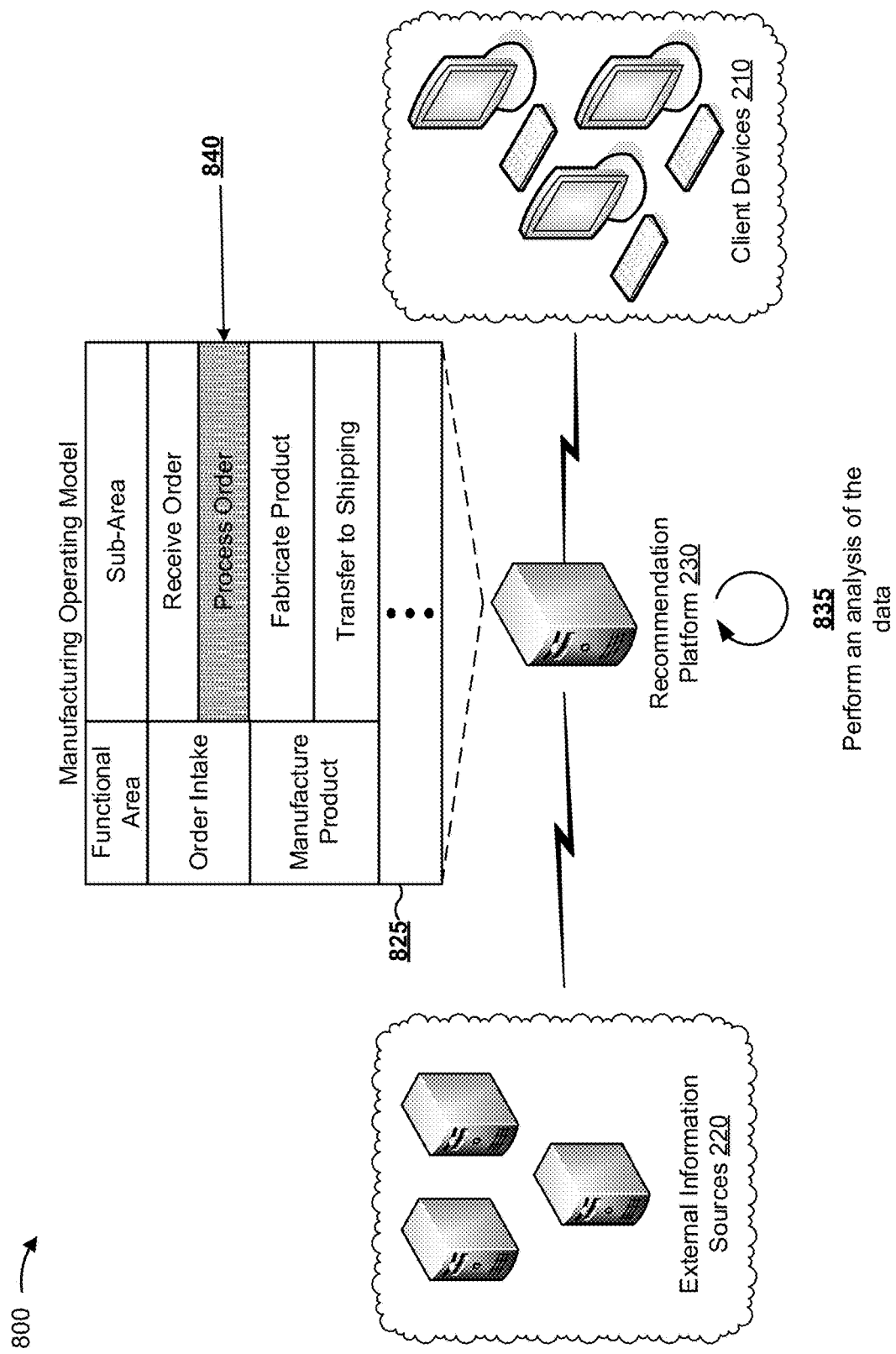

As shown in FIG. 8C, and by reference number 835, recommendation platform 230 may perform an analysis of the data to identify a deficiency related to implementation of the process and/or operations (e.g., by identifying sub-areas missing from implementation of the process and/or operations). As shown by reference number 840, recommendation platform 230 may identify a sub-area that is missing from implementation of the process (e.g., process order), as shown as a lightly shaded rectangle. In this way, recommendation platform 230 may identify a deficiency related to a process and/or operations of a manufacturing organization and/or a manner in which to improve the process and/or operations.

Figure 8D:
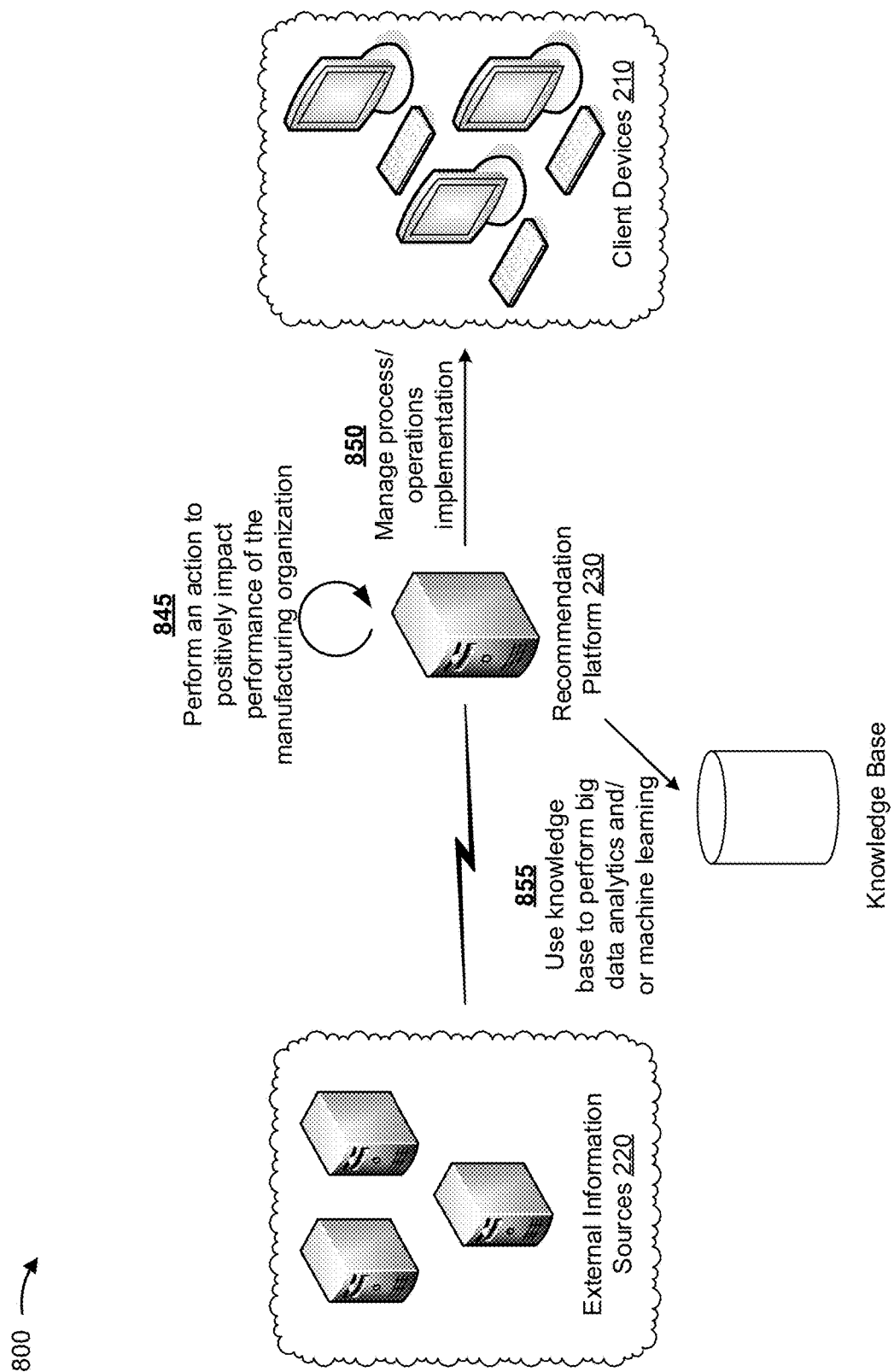

As shown in FIG. 8D, and by reference number 845, recommendation platform 230 may perform an action to positively impact performance of the manufacturing organization (e.g., generate a recommendation, send a message, schedule a meeting, etc., to improve a process and/or operations of the manufacturing organization). As shown by reference number 850, recommendation platform 230 may manage implementation of a process and/or operations of a manufacturing organization (e.g., based on the analysis and/or action). As shown by reference number 855, recommendation platform 230 may use a knowledge base to perform big data analytics and/or machine learning using data from the analysis, data gathered when managing implementation of the process and/or operations, and/or the like.

As indicated above, FIGS. 8A-8D are provided merely as an example. Other examples are possible and may differ from what was described with regard to FIGS. 8A-8D. In addition, although example implementations 500 through 800 were described as separate examples, example implementations 500 through 800 can occur concurrently.

Implementations described herein provide a recommendation platform that is capable of receiving data associated with a performance of a process of a PBM and/or specialty PBM organization and/or operations of the PBM and/or specialty PBM organization, analyzing the data to identify a deficiency related to the performance and/or a manner in which the performance can be improved, and/or automatically performing an action to positively impact the deficiency and/or to improve the performance.

In this way, some implementations, described herein, increase an efficiency of analyzing a process of a PBM and/or specialty PBM organization and/or operations of the PBM and/or specialty PBM organization. In addition, some implementations, described herein, improve an accuracy of a result and/or output of a process, thereby conserving processing resources that would otherwise be consumed due to inaccurate results and/or outputs. Further, some implementations, described herein, improve performance of a process and/or operations of a PBM and/or specialty PBM organization, thereby conserving processing resources and/or computing resources of devices used to implement the process and/or the operations.

Although implementations were described with respect a PBM and/or specialty PBM organization, the implementations apply equally to other types of organizations, such as non-PBM and/or non-specialty PBM organizations that are performing PBM and/or specialty PBM-like functions, information technology organizations, manufacturing organizations, and/or the like.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more processors to:
receive data associated with an organization,
the data relating to a performance of a process or operations of the organization,
the data relating to hardware resources of the organization used to implement the process or the operations;
identify, based on processing the data, metadata associated with the data,
the metadata being used to identify a type of the organization with which the data is associated,
the type including at least one of:
a pharmacy benefit manger (PBM) organization, or
a specialty PBM organization;
determine, based on identifying the metadata associated with the data, the type of the organization;

select, based on determining the type of the organization, an operating model to use to perform an analysis of the data,
the operating model including at least one of:
a PBM operating model associated with the PBM organization, or
a specialty PBM operating model associated with the specialty PBM organization;
map the data to the operating model based on processing the data,
the operating model to be used to compare the organization to one or more other organizations;
perform the analysis of the data based on mapping the data to the operating model;
identify an infrastructure of the organization based on performing the analysis of the data;
identify a deficiency related to at least one of the performance of the organization or the infrastructure of the organization based on identifying the infrastructure; and
configure, in real-time and based on the identified deficiency, at least one of:
another device associated with the organization, or
software to be online or offline.

2. The device of claim 1, where the one or more processors, when identifying the infrastructure, are to:
identify the infrastructure of the organization based on performing the analysis,
the infrastructure of the organization including at least one of:
a quantity of call centers associated with the organization,
a quantity of departments of the organization, or
a quantity of claims processing centers of the organization.

3. The device of claim 1, where the one or more processors, when receiving the data, are to:
receive cross-domain data associated with multiple types of organizations,
the cross-domain data including data elements related to other organizations associated with one or more other industries different than an industry associated with the organization; and
where the one or more processors are further to:
generate the operating model based on the cross-domain data.

4. The device of claim 1, where the one or more processors are further to:
identify a metric or a rule associated with the organization based on mapping the data to the operating model,
the metric or the rule to be used when performing the analysis; and
where the one or more processors, when performing the analysis, are to:
perform the analysis based on identifying the metric or the rule.

5. The device of claim 1, where the one or more processors, when mapping the data, are to:
map the data to the operating model to identify a manner in which an individual interacts with the organization; and
where the one or more processors, when performing the analysis, are to:
perform the analysis to identify the deficiency related to the manner in which the individual interacts with the organization based on mapping the data to the operating model.

6. The device of claim 1, where the one or more processors are further to:
receive other data associated with a manufacturing organization in association with receiving the data; and
where the one or more processors, when mapping the data, are to:
map the data to a manufacturing operating model based on receiving the other data.

7. A method, comprising:
receiving, by a device, data associated with a benefit manager organization,
the data relating to at least one of:
a process implemented by the benefit manager organization, or
operations of the benefit manager organization;
processing, by the device, the data using a technique to permit an analysis of the data after receiving the data,
the technique to be used to format the data to permit mapping or analysis of the data;
identifying, by the device and based on processing the data, metadata associated with the data,
the metadata being used to identify a type of the benefit manager organization with which the data is associated,
the type including at least one of:
a pharmacy benefit manger (PBM) organization, or
a specialty PBM organization;
determining, by the device and based on identifying the metadata associated with the data, the type of the benefit manager organization;
selecting, by the device and based on determining the type of the organization, a benefit manager operating model to use to perform the analysis of the data,
the benefit manager operating model including at least one of:
a PBM operating model associated with the PBM organization, or
a specialty PBM operating model associated with the specialty PBM organization;
mapping, by the device, the data to the benefit manager operating model based on processing the data,
the benefit manager operating model to be used to perform the analysis of the benefit manager organization,
the benefit manager operating model being associated with one or more other benefit manager organizations;
performing, by the device, the analysis of the data based on mapping the data to the benefit manager operating model;
identifying, by the device, an infrastructure of the organization based on performing the analysis;
identifying, by the device, a deficiency related to at least one of the performance of the organization or the infrastructure of the organization based on identifying the infrastructure; and
configuring, by the device, in real-time, and based on the identified deficiency, at least one of a device associated with the organization or software to be online or offline.

8. The method of claim 7, where processing the data comprises:
processing the data to identify a manner in which the benefit manager organization implements the process or the operations after receiving the data; and where performing the analysis further comprises:
performing the analysis of the manner in which the benefit manager organization implements the process or the operations based on processing the data.

9. The method of claim 7, further comprising:
receiving other data associated with the one or more other benefit manager organizations prior to receiving the data associated with the benefit manager organization;
identifying one or more functional areas or one or more sub-areas with which the other data is associated after receiving the other data;
generating, after receiving the other data and based on identifying the one or more functional areas or the one or more sub-areas, the benefit manager operating model; and
where receiving the data comprises:
receiving the data after generating the benefit manager operating model.

10. The method of claim 7, where identifying the deficiency is based on identifying a functional area or a sub-area that the benefit manager organization is missing based on mapping the data to the benefit manager operating model.

11. The method of claim 7, further comprising:
monitoring, based on configuring the other device or the software, the process or the operations.

12. A non-transitory computer-readable medium storing instructions, the instructions comprising:
one or more instructions that, when executed by one or more processors, cause the one or more processors to:
receive data associated with one or more benefit manager organizations,
the data relating to a performance of the one or more benefit manager organizations, and
the data relating to one or more hardware resources associated with the one or more benefit manager organizations;
identify, based on processing the data, metadata associated with the data,
the metadata being used to identify one or more types of the one or more benefit manager organizations with which the data is associated,
the one or more types including at least one of:
a pharmacy benefit manger (PBM) organization, or
a specialty PBM organization;
determine, based on identifying the metadata associated with the data, the one or more types of the one or more benefit manager organizations;
select, based on determining the one or more types of the one or more benefit manager organizations, one or more benefit manager operating models to use to perform one or more analyses of the data,
a benefit manager operating model of the one or more benefit manager operating models including at least one of:
a PBM operating model associated with the PBM organization, or
a specialty PBM operating model associated with the specialty PBM organization;
map the data to the one or more benefit manager operating models based on processing the data,
the one or more benefit manager operating models identifying one or more functional areas or one or more sub-areas of one or more other benefit manager organizations;
perform the one or more analyses of the data based on mapping the data to the one or more benefit manager operating models;
identify an infrastructure of the one or more benefit manager organizations based on performing the one or more analyses;
identify one or more deficiencies related to at least one of the performance of the one or more benefit manager organizations or the infrastructure of the one or more benefit manager organizations based on identifying the infrastructure; and
configure, in real-time and based on the one or more identified deficiencies, at least one of:
a device associated with the organization, or
software to be online or offline.

13. The non-transitory computer-readable medium of claim 12, where the one or more instructions, that cause the one or more processors to map the data, cause the one or more processors to:
map the data to identify the infrastructure of the one or more benefit manager organizations; and
where the one or more instructions, that cause the one or more processors to identify the one or more deficiencies, cause the one or more processors to:
identify the one or more deficiencies related to the infrastructure of the one or more benefit manager organizations based on mapping the data.

14. The non-transitory computer-readable medium of claim 12, where the one or more instructions, when executed by the one or more processors, further cause the one or more processors to:
determine one or more identifiers associated with the data based on processing the data,
the one or more identifiers identifying the one or more functional areas, or the one or more sub-areas, with which the data is associated; and
where the one or more instructions, that cause the one or more processors to map the data, further cause the one or more processors to:
map the data to the one or more functional areas or the one or more sub-areas of the one or more benefit manager operating models based on determining the one or more identifiers.

15. The non-transitory computer-readable medium of claim 12, where the one or more instructions, when executed by the one or more processors, further cause the one or more processors to:
provide information associated with the one or more analyses to one or more devices, including the device, to permit the one or more devices to perform one or more other analyses of the one or more other benefit manager organizations.

16. The non-transitory computer-readable medium of claim 12, where the one or more instructions, when executed by the one or more processors, further cause the one or more processors to:
generate one or more recommendations related to positively impacting the performance of the one or more benefit manager organizations based on performing the one or more analyses,
the one or more recommendations relating to the infrastructure or the one or more hardware resources of the one or more benefit manager organizations;
generate one or more scores for the one or more recommendations based on generating the one or more recommendations; and determine whether to configure the device or the software based on the one or more scores for the one or more recommendations.

17. The method of claim 7, wherein the data is mapped using at least one of:
   information identifying a previous mapping, or
   artificial intelligence.

18. The device of claim 1, where the one or more processors are further to:
   monitor, based on configuring the other device or the software, the process or operations.

19. The non-transitory computer-readable medium of claim 12, where the one or more instructions, when executed by the one or more processors, further cause the one or more processors to:
   monitor, based on configuring the other device or the software, the performance of the one or more benefit manager organizations.

20. The non-transitory computer-readable medium of claim 12, where the data is mapped using at least one of:
   information identifying a previous mapping, or
   artificial intelligence.

\* \* \* \* \*